(12) United States Patent
Nguyen et al.

(10) Patent No.: US 9,737,395 B2
(45) Date of Patent: Aug. 22, 2017

(54) SYSTEMS AND METHODS FOR REDUCING SCARRING

(71) Applicants: Phi Nguyen, Houston, TX (US); Loc Phan, San Jose, CA (US); Bao Tran, Saratoga, CA (US)

(72) Inventors: Phi Nguyen, Houston, TX (US); Loc Phan, San Jose, CA (US); Bao Tran, Saratoga, CA (US)

( * ) Notice: Subject to any disclaimer, the term of this patent is extended or adjusted under 35 U.S.C. 154(b) by 0 days.

(21) Appl. No.: 14/751,396

(22) Filed: Jun. 26, 2015

(65) Prior Publication Data
US 2016/0374798 A1    Dec. 29, 2016

(51) Int. Cl.
| A61F 2/12 | (2006.01) |
| A61F 2/00 | (2006.01) |
| A61L 27/34 | (2006.01) |
| A61L 27/50 | (2006.01) |
| A61L 27/54 | (2006.01) |

(52) U.S. Cl.
CPC .............. *A61F 2/12* (2013.01); *A61F 2/0077* (2013.01); *A61L 27/34* (2013.01); *A61L 27/50* (2013.01); *A61L 27/54* (2013.01); *A61F 2002/0091* (2015.04); *A61F 2210/0004* (2013.01); *A61F 2210/0076* (2013.01); *A61F 2250/0067* (2013.01); *A61L 2300/416* (2013.01); *A61L 2400/18* (2013.01)

(58) Field of Classification Search
CPC ..... A61F 2/0077; A61F 2/12; A61L 2300/236
See application file for complete search history.

(56) References Cited

U.S. PATENT DOCUMENTS

| 3,293,663 | A | 12/1966 | Cronin |
| 5,346,480 | A | 9/1994 | Hess |
| 5,480,430 | A | 1/1996 | Carlisle |
| 5,545,217 | A | 8/1996 | Offray |
| 5,827,937 | A | 10/1998 | Agerup |
| 5,941,909 | A | 8/1999 | Purkait |
| 6,096,727 | A | 8/2000 | Kuo |
| 6,117,444 | A | 9/2000 | Orgill |
| 6,548,081 | B2 | 4/2003 | Sadozai |
| 6,638,308 | B2 | 10/2003 | Corbitt |
| 6,703,444 | B2 | 3/2004 | Zhao |
| 6,955,690 | B1 | 10/2005 | Cao |
| 7,081,136 | B1 | 7/2006 | Becker |
| 7,156,837 | B2 | 1/2007 | Agerup |
| 7,160,931 | B2 | 1/2007 | Cheng |
| 7,278,985 | B2 | 10/2007 | Agerup |
| D611,594 | S | 3/2010 | Ratjen |
| 7,741,476 | B2 | 6/2010 | Lebreton |
| 7,942,930 | B2 | 5/2011 | Agerup |
| 7,951,880 | B2 | 5/2011 | Lim |
| 8,043,373 | B2 | 10/2011 | Schuessler |
| 8,070,808 | B2 | 12/2011 | Maxwell |

(Continued)

*Primary Examiner* — David Isabella
*Assistant Examiner* — Dinah Baria
(74) *Attorney, Agent, or Firm* — Tran & Associates

(57) ABSTRACT

Systems and methods are disclosed to protect a medical device from scarring a body after implanting the device in the body by creating a bonding matrix on a surface of the device; exposing the surface to hyaluronic acid (HA) or polyethylene glycol (PEG); cross linking the HA or PEG; and preventing capsular contracture after implanting the device in the body.

15 Claims, 5 Drawing Sheets

(56) References Cited

U.S. PATENT DOCUMENTS

| | | | |
|---|---|---|---|
| 8,414,907 B2* | 4/2013 | Molz | A61L 27/34 |
| | | | 424/423 |
| 8,628,790 B2 | 1/2014 | To | |
| 2005/0226936 A1 | 10/2005 | Agerup | |
| 2007/0135916 A1 | 6/2007 | Maxwell | |
| 2008/0312739 A1 | 12/2008 | Agerup | |
| 2009/0155362 A1 | 6/2009 | Longin | |
| 2010/0119578 A1 | 5/2010 | To | |
| 2010/0261893 A1 | 10/2010 | Chen | |
| 2011/0276135 A1 | 11/2011 | Yacoub | |

* cited by examiner

| creating a bonding matrix on a surface of the device (1) |
| exposing the surface to hyaluronic acid (HA) or polyethylene glycol (PEG) (2) |
| cross linking the HA or PEG (3) |
| preventing capsular contracture after implanting the device in the body (4) |

SYSTEMS AND METHODS FOR REDUCING SCARRING

The present invention relates to reduction of scarring due to placement of an implant or device in the human body.

Breast implants and methods for breast reconstruction and augmentation are well known and have been used for a period of over twenty years. One issue arising with the use of breast implants is the formation of excess scar tissue around an implant. Such tissue can harden and lead to tightening around or squeezing of the implant, a phenomenon known as capsular contracture. While scar tissue and capsule formation is a normal process, when scar tissue is excessive the subsequent capsule is called capsular contracture and can lead to an implant that is misshapen, painful, hard and can attain an unnatural appearance and feel. Additionally, capsular contracture appears to be more common following infection, hematoma and seroma. The reason for capsular contracture is not well-defined. Implant infection is most commonly attributed to contamination of the sterile field during surgery or to contamination arising from lymph node or mammary duct dissection during surgery. Bacteria can migrate deep within the breast tissue via the mammary ducts. Incision through the ducts during subglandular placement thus opens a temporary but direct external route for contamination of the implant after placement. Bacteria colonized from the mammary ducts and nipples is similar to exogenous flora found on the skin, namely coagulase negative *Staphylococcus*, *P. acne*, and *Bacillus subtillus*.

Subclinical infection is perceived to be a contributor to capsular contracture. Subclinical infection is defined as bacterial colonization of a surface with or without biofilm formation. It does not produce the signs and symptoms traditionally associated with frank infection (such as pain, tenderness, fever, and pus) and manifests itself as a chronic inflammatory response. This inflammatory response leads to an overaggressive collagen deposition during tissue remodeling that leads to fibrous tissue buildup and capsule rigidity with eventual implant distortion.

Most surgeons engage in prophylactic efforts to reduce the incidence of infection associated with breast implants, including a no-touch technique by the surgeon. For example, in addition to meticulous attention to sterility, many surgeons irrigate the implant pocket and bathe the implant itself with gentamycin, cefazolin, povidone-iodine or another antibiotic solution. Post-operative counseling includes instructing the patient to neither touch the incision sites nor to immerse them in hot water for at least two weeks (or until healing is complete). Prophylactic oral antibiotics can also be given to patients prior to, during and after surgery to prevent post-implant colonization. Additionally, implant placement below the muscle avoids (or at least minimizes) surgical contact with the mammary ducts.

Texturing the outside silicone surface has been employed as a technique to prevent capsular contracture. The textured surface causes a disorganization of collagen during deposition which minimizes capsule contracture. However, these implants have not significantly penetrated the market because, in use, tissue adherence to the textured surface leads to visible dimpling effect when the recipient moves. Textured implants also tend to have thicker shells than smooth implants and higher rupture rates.

The partial or total adhesion of the implant to the capsule due to such tissue ingrowth may be undesirable in the event it becomes necessary to remove or replace the implant. Notwithstanding the foregoing disadvantages, textured implants having a biocompatible, non-bioabsorbable outer tissue-contacting surface are generally considered to reduce the incidence of capsular contracture in patients.

There remains a need for an implantable filled breast prosthesis, typically filled with silicone gel or saline solution, with or without gas pockets, that resists capsular contracture following implantation and that resists adherence of the implant to the capsule.

In a parallel trend, surgical adhesions are abnormal, fibrous bands of scar tissue that can form inside the body as a result of the healing process that follows any open or minimally invasive surgical procedure including abdominal, gynecologic, cardiothoracic, spinal, plastic, vascular, ENT, opthalmologic, urologic, neuro, or orthopedic surgery. Surgical adhesions are typically connective tissue structures that form between adjacent injured areas within the body. Briefly, localized areas of injury trigger an inflammatory and healing response that culminates in healing and scar tissue formation. If scarring results in the formation of fibrous tissue bands or adherence of adjacent anatomical structures (that should be separate), surgical adhesion formation is said to have occurred. Adhesions can range from flimsy, easily separable structures to dense, tenacious fibrous structures that can only be separated by surgical dissection. While many adhesions are benign, some can cause significant clinical problems and are a leading cause of repeat surgical intervention. Surgery to breakdown adhesions (adhesiolysis) often results in failure and recurrence because the surgical trauma involved in breaking down the adhesion triggers the entire process to repeat itself.

SUMMARY

Systems and methods are disclosed to protect a medical device from scarring a body after implanting the device in the body by grafting onto the surfaces of the device ubiquitous ECM (extra cellular matrix) materials so that the device may appear native and not foreign to the body and then causing a foreign body response. These extra cellular matrix materials for example are Proteoglycans and Non-Proteglycans, Chondroitin Sulfate, Heparan sulfate and Keratan sulfate. The ECM fiberous materials such as collagen, elastin fibronectin and lamilin also are candidate materials. A medical implant covered with such ECM material would not easily be recognized by the body as foreign body and thus is prevention against capsular contracture after the device is implanted.

In another aspect, portions of a breast prosthesis, or prostheses for other applications, may be coated and configured to promote endothelization/healing by substantially blocking elution of antiproliferative drugs, before controllably eluting drugs to prevent excessive cellular encapsulation and/or adhesion.

Advantages of the invention may include one or more of the following. The system minimizes tissue scarring for implantable medical devices. Moreover, a natural feel is achieved through viscoelastic harmony of properties between the existing tissue and the implant. This is done by manipulating the viscous component of the implant through flow properties by way of the particle size and particle size distribution ratios. The elastic component is intrinsic within the material tertiary structure (molecular weight and steric hindrance) and cross linking densities. The interpenetrating polymer network hydrogels have a number of desirable properties. These properties include high tensile strength with high water content, making the interpenetrating polymer network hydrogels excellent for use in dermal filling applications. Other advantages and features include: longevity without touch up, hyper-volumic degradation, anatomic compliant and iso-osmotic controlled, among others.

These and other aspects of the present invention will become evident upon reference to the following detailed description and attached drawings. In addition, various references are set forth herein which describe in more detail certain procedures and/or compositions (e.g., polymers), and are therefore incorporated by reference in the entirety.

DESCRIPTION

As used herein, the singular forms "a", "an", and "the" include plural referents, and plural forms include the singular. "Antiproliferative" is used to refer to a substance that has the effect of inhibiting thickening, volume, or mass growth of tissue generally, including in the space surrounding an implant. The term includes "antirestenosis" and extracellular matrix-suppressing. The term may used in association with therapeutic agents and/or therapeutic agents and if not otherwise specified refers to both therapeutic agents and therapeutic agents and any other substance that have the given effect. "Antirestenosis" is used to refer to a substance that has the effect of inhibiting thickening, volume, or mass growth of tissue that would otherwise restrict a passageway within a lumen or vessel, including tissue development on an implant, such as a stent, that would thereby decrease the inner diameter of a vessel in which the implant is positioned. "Coating" is used to refer to a layer on an implant, such as a stent, that is comprised of material different than the struts and fibers of the stent and may or may not include a therapeutic agent incorporated therein. "Drug" is used to refer to classical pharmaceutical therapeutic agents which typically are represented by complex chemical formulae. It includes brandname drugs, generic drugs, and any later-discovered compounds that may be found to have effects similar or superior to those of currently known drugs. "Matrix" is used to refer to a structural framework of something. It may be used to describe the basic structure of a stent of a coating layer upon a stent. The matrix may or may not include a therapeutic agent incorporated therein. "Therapeutic agent" is used to refer to any material, substance, compound, factor, chemical, biological composition, drug, etc. that has a beneficial effect. It includes both naturally occurring and synthetic materials. The beneficial or therapeutic effect includes but is not limited to: suppressing an ECM component, inhibiting restenosis, preventing clotting, preventing thrombosis, suppressing excessive proliferation or one or more tissue type, encouraging synthesis/migration/aligned deposition of endothelial cells, etc. referent unless the context clearly dictates otherwise.

Figures 1A, 1B:
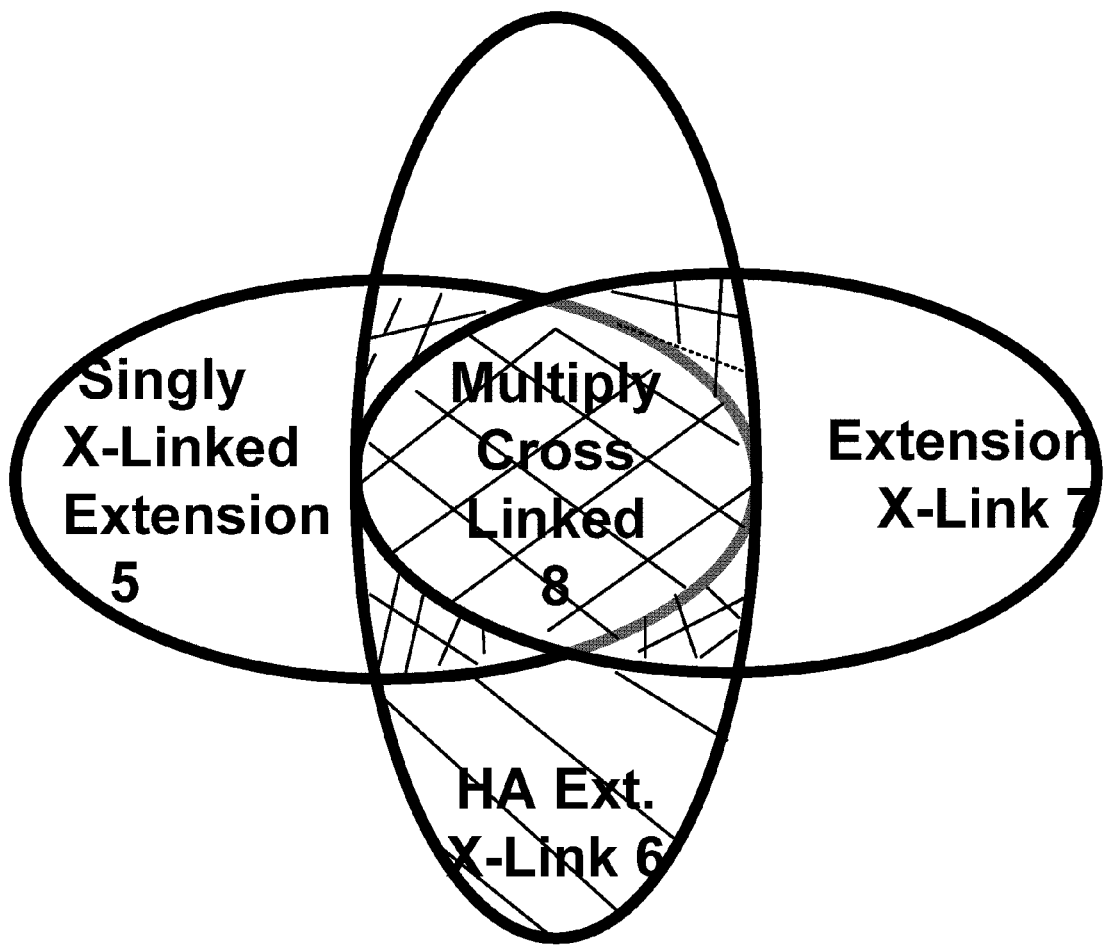
FIG. 1A shows an exemplary system to protect a body from scarring associated with a medical device.
FIG. 1B shows an multiply cross-linked HA.

FIG. 1A shows an exemplary process to protect a medical device from scarring a body after implanting the device in the body by: creating a bonding matrix on a surface of the device (1), exposing the surface to hyaluronic acid (HA) or polyethylene glycol (PEG) (2), cross linking the HA or PEG (3), preventing capsular contracture after implanting the device in the body (4).

The term "hyaluronic acid" is used to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs. The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term. HA can also be defined as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein. More details on how to make the HA are discussed in commonly owned, co-pending application Ser. No. 13/353,316, filed Jan. 18, 2012, and entitled "INJECTABLE FILLER," the content of which is incorporated by reference.

PEG, PEO, or POE refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass.[2] PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete. Very high purity PEG has recently been shown to be crystalline, allowing determination of a crystal structure by x-ray diffraction.[3] Since purification and separation of pure oligomers is difficult, the price for this type of quality is often 10-1000 fold that of polydisperse PEG.

The chemical cross linking agent can be divinyl sulfide (DVS) or butanediol diglycidyl ether (BDDE).

| | grams*/mL** |
|---|---|
| Primer Step | |
| 1. Make Mix | |
| Silicone breast implant shell material | 7.001 |
| Plasticizing Solvent** | 10 |

-continued

|  | grams*/mL** |  |
|---|---|---|
| 2-Hydroxy Ethyl Methacrylate* | 3 | |
| AIBN | 0.025 | |
| Let stand for 1 hour | | |
| 2. Reaction | | |
| Remove silicone shell material from mixture | | |
| Let drain | | |
| Place mixture into a pyrex glass bottle | | |
| Purge the bottle environment so that it is free of oxygen | | |
| Place into oven at 60 C. for 1 hour | | |
| 3. Clean up | | |
| Ethanol** | 20 | |
| Place the silicone shell into ethanol | | |
| Let stand for 1 hour; exchange the ethanol every 15 min. | | |
| 4. Measure | | |
| Dry the gel for 2 hours at 80 C. | | |
| Weight the gel | 7.057 | 0.80% |
| Place the gel into DI water | | |
| Weight the gel hydrated | 7.105 | 1.49% |
| HA Incorporation Step | | |
| 1. Make Mix | | |
| Silicone breast implant shell material | 7.057 | |
| Plasticizing Solvent** | 10 | |
| HA in NaOH @ 10%** | 5 | |
| Let stand for 1 hour | | |
| 2. Reaction | | |
| Remove silicone shell material from mixture | | |
| Let drain | | |
| Place mixture into a pyrex glass bottle | | |
| Purge the bottle environment so that it is free of oxygen | | |
| Place into oven at 60 C. for 1 hour | | |
| 3. Clean up | | |
| Ethanol** | 20 | |
| Place the silicone shell into ethanol | | |
| Let stand for 1 hour; exchange the ethanol every 15 min. | | |
| 4. Measure | | |
| Dry the gel for 2 hours at 80 C. | | |
| Weight the gel | 7.089 | 0.45% |
| Place the gel into DI water | | |
| Weight the gel hydrated | 7.301 | 3.46% |

In one embodiment, the HA can be serially cross-linked to form a system with monophasic characteristics. The forming a biocompatible cross-linked polymer as an IPN can be done by cross-linking a heteropolysaccharide to form a single cross-linked material; and performing one or more additional cross-linkings on the single cross-linked material to form a multiple cross-linked material, wherein the multiple cross-linked material has a core that lasts longer in a human body than the single cross-linked material. The result is a material with a smooth continuum from slightly cross-linked to the core which is highly cross-linked. The slightly cross-linked material enables the HA to be easily inserted into the human body with a small gauge syringe, but such slightly cross-linked material will not last long in the human body. However, the highly cross-linked material will remain longer in the human body so that the body augmentation does not need periodic touch-ups as is needed by conventional HA dermal fillers. The HA can be cross-linked to an iso-osmotic state.

The cross-link time resulting from the use of a stable, non-aqueous suspension of a delayed cross-linker according to the preferred embodiment may be controlled by varying any one or all of the following:
1) the cross linking compound used,
2) the particle size of the HA in suspension,
3) the pH of the fluid containing the HA,
4) the concentration (i.e., loading) of the HA suspension,
5) the temperature of the solution.

Illustratively, when used under similar conditions, the type of molecular weight of the HA compound may be employed effectively to control the exact cross-linking time of the water-soluble solution. More particularly, suspensions of larger molecular weight HA cross-link more slowly than suspensions of low molecular weight acid.

With respect to the particle size of the suspended halyuronic acid, as particle size increases, the time required for the cross-linking of a water-soluble polymer solution increases. Conversely, as the particle size decreases, the time required for the cross-linking of a water soluble decreases.

The pH of the water soluble polymer solution prior to its cross-linking may be used to control cross-link time. The pH of the water soluble polymer solution affects the solubility rate of the stable, non-aqueous suspension of a delayed cross-linker. Specifically, as the pH of the water soluble polymer solution increases, the solubility rate of the cross-linker suspension increases if the suspension contains a majority of HA particles, whereas the solubility rate of the cross-linker suspension decreases if the suspension contains a majority of borax particles. Conversely, as the pH of the water soluble polymer solution decreases, the solubility rate of the cross-linker suspension decreases if the suspension contains a majority of boric acid particles, whereas the solubility rate of the cross-linker suspension increases if the suspension contains a majority of HA particles.

Both the concentration (i.e., loading) of the stable, non-aqueous suspension of a delayed HA cross-linker in the water soluble polymer solution and the content of the cross-linker suspension affect the cross-link time of a water soluble polymer solution similarly. As either the concentration of the suspension of delayed HA cross-linker in the water-soluble polymer solution or the content of the cross-linker suspension increase, the cross-link time of the water soluble polymer solution decreases. Conversely, as either the concentration of the suspension of the delayed boron cross-linker in the water soluble polymer solution and the content of the cross-linker suspension decrease, the cross-link time of the water soluble polymer solution increases.

Temperature may be used to alter the cross-link time of a water soluble polymer solution. As the temperature of the water soluble polymer solution increases, its cross-link time decreases. Conversely, as the temperature of the water soluble polymer solution decreases, its cross-link time increases. Furthermore, the cross-link time of a water-soluble polymer may be increased or decreased depending upon the clay type utilized in the formulation of the stable, non-aqueous suspension of a delayed HA cross-linker.

In addition, materials such as polymeric microspheres, polymer micelles, soluble polymers and hydrogel-type materials can be used for providing protection for pharmaceuticals against biochemical degradation, and thus have shown great potential for use in biomedical applications, particularly as components of drug delivery devices. The design and engineering of biomedical polymers (e.g., polymers for use under physiological conditions) are generally subject to specific and stringent requirements. In particular, such polymeric materials must be compatible with the biological milieu in which they will be used, which often means that they show certain characteristics of hydrophilicity. They also have to demonstrate adequate biodegradability (i.e., they degrade to low molecular weight species. The polymer fragments are in turn metabolized in the body or excreted, leaving no trace). Biodegradability is typically accomplished by synthesizing or using polymers that have hydrolytically unstable linkages in the backbone. The most common chemical functional groups with this characteristic are esters, anhydrides, orthoesters, and amides. Chemical hydrolysis of the hydrolytically unstable backbone is the prevailing mechanism for the degradation of the polymer. Biodegradable polymers can be either natural or synthetic. Synthetic polymers commonly used in medical applications and biomedical research include polyethyleneglycol (pharmacokinetics and immune response modifier), polyvinyl alcohol (drug carrier), and poly(hydroxypropylmetacrylamide) (drug carrier). In addition, natural polymers are also used in biomedical applications. For instance, dextran, hydroxyethylstarch, albumin and partially hydrolyzed proteins find use in applications ranging from plasma substitute, to radiopharmaceutical to parenteral nutrition. In general, synthetic polymers may offer greater advantages than natural materials in that they can be tailored to give a wider range of properties and more predictable lot-to-lot uniformity than can materials from natural sources.

As shown in FIG. 1B, the HA can form an interpenetrating network to resist biodegration. FIG. 1B shows an exemplary diagram of the resulting multiply cross-linked HA. The composition includes a first portion 5 of a first polymer with lightly cross-linking extensions or arms; a second portion 6 of polymer with a first serially cross-linked center overlapping the first portion and one or more lightly cross-linked extensions adjacent the serially cross-linked center; and a third portion 7 of polymer with a second serially cross-linked region 8 overlapping the second portion and one or more lightly cross-linked extensions adjacent the serially cross-linked center; wherein the lightly cross-linked extensions enable the composition to be injected through a small gauge needle and the second serially cross-linked center is resistant to absorbtion by biological processes. The region 8 can be multiply cross-linked for biodegradation resistance. The polymer can be one of: collagens, hyaluronic acids, celluloses, proteins, saccharides, an extracellular matrix of a biological system.

In another embodiment, a biocompatible cross-linked IPN polymer can be done by cross-linking a heteropolysaccharide to form a first cross-linked material; and by performing one or more additional cross-linking of the first cross-linked material to form a multiple cross-linked material. The result monophasic HA can be used for augmenting soft tissue with the biocompatible cross-linked polymer.

Besides the foregoing methods of obtaining IPN and semi-IPN by crosslinking both of the components of the blend, semi-IPN can also be obtained by the polymerization of a monomer in the presence of a crosslinking agent and in the presence of the natural acidic polysaccharide or a semi-synthetic ester-type derivative thereof.

Figure 2:
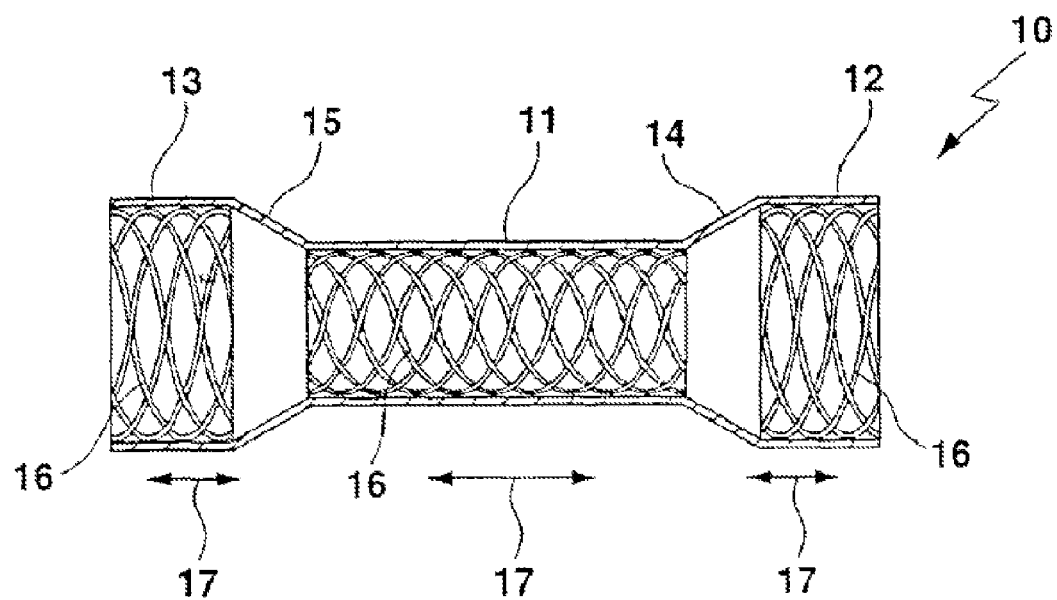
FIG. 2 shows an exemplary stent protected by the process of FIG. 1A.

FIG. 2 shows a stent 10 which is formed from a first stent section 11, a second stent section 12, a third stent section 13, a first elastic tubular section 14 and a second elastic tubular section 15. The stent 10 is shown in an unloaded expanded state. The support construction in the stent sections 11, 12, 13 is a web 16 which may be tubularly braided or woven. The individual filaments of the web may be produced from metal, plastic or carbon which is protected using the process of FIG. 1. The first stent section 11 may be the tubular web 16 itself or the web 16 is additionally surrounded by a plastic jacket. The gaps (meshes) of the web 16 may be open or closed. The second and third stent section 12, 13 have a larger diameter than the first stent section 11. The web 16 of the first stent section 11 was also chosen as support construction in the stent sections 12, 13. The diameters of the individual filaments of the web 16 in the stent sections 12, 13 may be different from the filament diameters of the filaments used in the first stent section 11. The stent sections 11-13 have filaments that are covered by an anti-scarring agent, which can be hyaluronic acid (HA) or polyethylene glycol (PEG), for example. In one embodiment, the filaments of the stent 10 is treated by creating a bonding matrix on a surface of the device; exposing the surface to hyaluronic acid (HA) or polyethylene glycol (PEG); cross linking the HA or PEG, where the HA or PEG prevents capsular contracture after implanting the device in the body.

The stent sections 11, 12, 13 are connected to each other via a first and second elastic tubular section 14, 15. The elastic tubular sections 14, 15 are produced from a flexible thin plastic material, e.g. silicon, and permanently and securely connect the stent sections 11, 12, 13. The elastic tubular sections 14, 15 can safely bridge diameter changes between the individual stent sections 11, 12, 13 and can adjust to the surface contour in a hollow organ without forming gaps. The stent 10 can be lengthened in the direction of arrows 17 and be shortened again after lengthening. The present case concerns an automatically expanding stent 10 which has a smaller diameter in the lengthened state than in the expanded state shown in the figure.

Figure 3A:
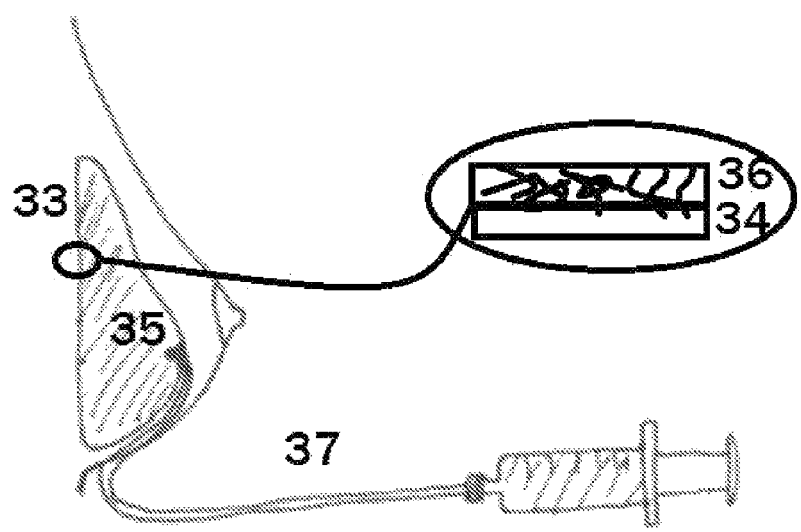
FIGS. 3A-3B show an exemplary breast implant protected by the process of FIG. 1A.
Figure 3B:
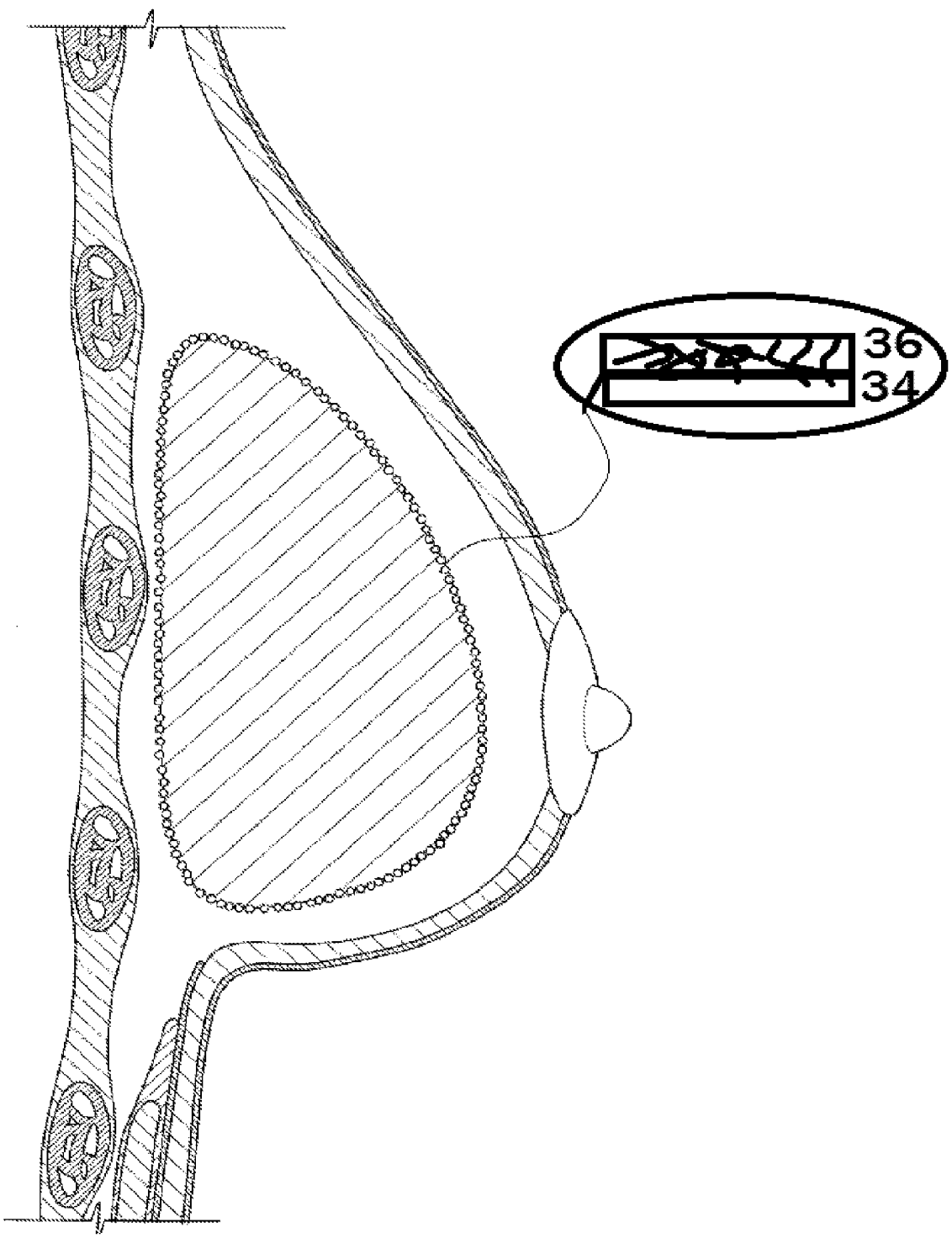

FIGS. 3A-3B shows an exemplary breast implant that is protected by the method of FIG. 1. The breast implants or prosthesis can be a single or multi-lumen device with an envelope of medical grade elastomer such as silicone sized and adapted to receive a quantity of silicone gel, saline or the like. Some implants also include a tissue expansion feature such as an expandable bladder or lumen with a local or remote port to add or remove liquid or gel. The soft pliable prosthetic implants included a smooth outer surface 34 with a protective layer of anti-scarring agent 36 such as HA or PEO, among others. As shown in FIG. 3B, some implants also include a tissue expansion feature such as an expandable bladder or lumen with a local or remote port to add or remove liquid or gel. The embodiments of FIGS. 3A-3B have an outer layer covered by the anti-scarring agents.

In one embodiment where the device is a breast implant, the method includes swelling an implant shell; allowing the HA to diffuse into a polymer matrix of the shell; crosslinking the HA while the shell is swollen; and deswelling the implant thereafter.

The shell can be swelled with THF or DCM. Tetrahydrofuran (THF) is an organic compound with the formula $(CH_2)_4O$. The compound is classified as heterocyclic compound, specifically a cyclic ether. It is a colorless, water-miscible organic liquid with low viscosity. Dichloromethane (DCM, or methylene chloride) is an organic compound with the formula $CH_2Cl_2$. This colorless, volatile liquid with a moderately sweet aroma is widely used as a solvent. The deswelling of the shell can be done with water or saline.

In one embodiment, the anti-scarring agents are partially impregnated into the outer layer of an implant and promote ingrowth of a body's tissue and blood vessels into the biologically active material between the implant bodies and the tissue to form a biological barrier between the patient's tissue and the silicone implant. Furthermore, a relatively strong bond between the patient's tissue and the implant may form. This reduces the likelihood of implant rotation and capsular contraction.

The anti-scarring agents are preferably applied to the final or outer coating before curing thereof. The silicon bag or shell is first expanded to provide cavities that the HA can fill. The HA is then cross-linked and a portion of the particles then project outwardly from the shell and provide an irregular topography having a plurality of irregular shaped cavities that are filled by portions of the HA particles in one embodiment. Any material used in the cross-linking of the HA is then extracted, and then the shell can be deflated and ready for use.

The HA particles are left embedded into the silicone rather than being dissolved out to result in a textured surface to decrease capsular contraction. Tissue then grows into the empty spaces after the bio-absorbable material is absorbed. The HA particles are not absorbed but rather become incorporated into the host tissue as a protective outer layer. HA provides a favorable environment for cell growth and motility that fosters tissue regeneration. Other ground substances such as polyglycans and materials from connective tissue may be used. The texturing of silicone implants prevents rotation of anatomical or shaped implants and that textured surfaces also decrease capsular contracture (hardening around the implant).

In another embodiment, in place of expanding the silicon and deflating the silicon to provide anchor points for the HA, the method includes placing salt on the surface of the silicone shell before drying and then dissolving the salt in water has been used. The cavities left by the salt create a textured surface. Various types of imprints can also be mechanically stamped on the surfaces of a shell before drying. In the present invention the above methods of texturing may be used to form a textured surface. The particles not only create a textured surface, but the silicone is partially concealed or protected from tissue ingrowth. The HA will adhere to the surrounding tissues and that covering tissue protect the patient from adhesions while preventing rotation and hardening. The intrinsic properties of the HA covering the implant add a new dimension of flexibility to large space augmentation such as that of the breast, body or the buttock.

In one aspect, systems and methods are disclosed for cosmetic augmentation of soft tissue using cross-linked HA that had been optimized for
1. ease of product delivery,
2. local tissue compliant,
3. greater cohesiveness to control migration of the implant material and
4. bio-degradation profile.

The use of a particularly cross linked HA, and cross linked by forming regions of interpenetrating network (IPN) of cross linked HA by further crosslinking them. The IPN configuration gives this cross linked HA those utilities unique for this cosmetic augmentation application. The IPN core (imagine a tapioca ball) is more resistance to biodegradation in a human body than the single cross-linked material normalized for the same cross linking level. Furthermore, varying physical properties that continuously changes radiating out from the core makes the polymer tough and at the same time compliant with the local tissue for better tissue/device biocompatibility and feels more natural to the touch.

The above HA cross linking method optimized for cosmetic augmentation in certain cases may need to control delivered pharmaceutical substances to modulate local tissue response to the polymer. The pharmaceutical component makes up the multi-phase mixture with the other phase being the cross linked HA polymer.

Implementations of the above aspects may include one or more of the following. The system is biocompatible and performs controlled drug releases at strategic timing to coincide with key physiological events. For example, a fast drug release profile and no delay would be well suited for the controlled release of an anesthetic such as lidocane to relieve acute pain experienced by the patient associated with the surgical procedure. The system is also capable of a medium release profile and a medium delay of a corticosteroid or steroid such as dexamethasone or triamcinolone to co-inside with a physiological inflammatory foreign body reaction. The system can also be customized to have a medium to slow release profile and a longer delay before starting the release of an antiproliferative drug such as paclitaxel, serolimas or 5-flourouracil to stop uncontrolled healing and excessive remodeling causing unsightly scar formation or capsular formation.

1. Molecular Weight Manipulation

Another aspect of the present invention includes methods for optimizing biodegradation profiles and control migration of the implant material through the manipulation of various types molecular weight. The system optimizes biodegradation profiles and controls migration of the implant material. The system can be formulated around various types of molecular weights such as $M_n$, $M_w$ and $M_z$, and their polydispersity index (PDI) to optimize the biodegradation profiles to be from hypervolumic to isovolumic to hypovolumic.

2. Free Radical Scavengers Vitamins and Enzymes

HA in the body is biodegraded by two major mechanisms: oxidative and hydrolytic. Inside the cell of mammals, the mechanism is enzymatic hydrolysis by three enzymes hyaluronidase (hyase), b-d-glucuronidase, and β-N-acetylhexosaminidase. and outside the cell the mechanism is oxidation by oxygen derived free radical, or sometimes, they are called reactive oxygen species (ROS). These are atoms or groups of atoms with an odd (unpaired) number of electrons and can be formed when oxygen interacts with certain molecules.

ROS are produced as a normal product of cellular metabolism. In particular, one major contributor to oxidative damage is hydrogen peroxide (H2O2), which is converted from superoxide that leaks from the mitochondria. Catalase and superoxide dismutase ameliorate the damaging effects of hydrogen peroxide and superoxide by converting these compounds into oxygen and water, benign molecules. However, this conversion is not 100% efficient, and residual peroxides persist in the cell. While ROS are produced as a product of normal cellular functioning, excessive amounts can cause deleterious effects. Memory capabilities decline with age, evident in human degenerative diseases such as Alzheimer's disease, which is accompanied by an accumulation of oxidative damage. Current studies demonstrate that the accumulation of ROS can decrease an organism's fitness because oxidative damage is a contributor to senescence. In particular, the accumulation of oxidative damage may lead to cognitive dysfunction, as demonstrated in a study in which old rats were given mitochondrial metabolites and then given cognitive tests. Results showed that the rats performed better after receiving the metabolites, suggesting that the metabolites reduced oxidative damage and improved mitochondrial function. Accumulating oxidative damage can then affect the efficiency of mitochondria and further increase the rate of ROS production. The accumulation of oxidative damage and its implications for aging depends on the particular tissue type where the damage is occurring. Additional experimental results suggest that oxidative damage is responsible for age-related decline in brain functioning. Older gerbils were found to have higher levels of oxidized protein in comparison to younger gerbils. Treatment of old and young mice with a spin trapping compound caused a decrease in the level of oxidized proteins in older gerbils but did not have an effect on younger gerbils. In addition, older gerbils performed cognitive tasks better during treatment but ceased functional capacity when treatment was discontinued, causing oxidized protein levels to increase.

Furthermore, once formed these highly reactive radicals can start a chain reaction. Their chief danger comes from the damage they can do when they react with important cellular components such as DNA, or the cell membrane. Cells may function poorly or die if this occurs. To prevent free radical damage the body has a defense system of antioxidants. The free radicals and the antioxidants react with one another readily and easily.

The degradation reaction by oxygen derived free radical of HA was the results of studies using the HA present in synovial fluids. It showed that the HA was readily degraded by super oxide free radicals. This reaction is most favorable in the case of secondary free radicals. Neutrophils (polymorphonuclear leukocytes) produced the type of oxygen derived free radicals that allowed it phagocytotically consumed HA molecules. These WBC's are by far the exclusive destroyers of HA by oxygen-derived free radical mechanism. Thus, an aspect of this invention is to quench the effect of the free radical before it degrades the HA using free radical scavengers such as antioxidant vitamins.

Antioxidants are intimately involved in the prevention of cellular damage—the common pathway for cancer, aging, and a variety of diseases. Antioxidants are molecules which can safely interact with free radicals and terminate the chain reaction before vital molecules are damaged. Although there are several enzyme systems within the body that scavenge free radicals, the principle micronutrient (vitamin) antioxidants are vitamin E, beta-carotene, and in the case of HA, vitamin C is the exception. Additionally, selenium, a trace metal that is required for proper function of one of the body's antioxidant enzyme systems, is sometimes included in this category. The body cannot manufacture these micronutrients so they must be supplied in the diet.

Following are example antioxidant vitamins, their roles and recommended daily dosages:

Vitamin E: d-alpha tocopherol. A fat soluble vitamin present in nuts, seeds, vegetable and fish oils, whole grains (esp. wheat germ), fortified cereals, and apricots. Current recommended daily allowance (RDA) is 15 IU per day for men and 12 IU per day for women.

Vitamin C: The exception in the case of HA as it is detrimental to the longevity of HA. However, vitamin C is ascorbic acid, and it is a water soluble vitamin present in citrus fruits and juices, green peppers, cabbage, spinach, broccoli, kale, cantaloupe, kiwi, and strawberries. The RDA is 60 mg per day. Intake above 2000 mg may be associated with adverse side effects in some individuals.

Vitamin A: Beta-carotene is a precursor to vitamin A (retinol) and is present in liver, egg yolk, milk, butter, spinach, carrots, squash, broccoli, yams, tomato, cantaloupe, peaches, and grains. Because beta-carotene is converted to vitamin A by the body there is no set requirement. Instead the RDA is expressed as retinol equivalents (RE), to clarify the relationship. (NOTE: Vitamin A has no antioxidant properties and can be quite toxic when taken in excess.)

Glutathione: (GSH) is a tripeptide with a gamma peptide linkage between the amine group of cysteine (which is attached by normal peptide linkage to a glycine) and the carboxyl group of the glutamate side-chain. It is an antioxidant, preventing damage to important cellular components caused by reactive oxygen species such as free radicals and peroxides. Thiol groups are reducing agents, existing at a concentration of approximately 5 mM in animal cells. Glutathione reduces disulfide bonds formed within cytoplasmic proteins to cysteines by serving as an electron donor. In the process, glutathione is converted to its oxidized form glutathione disulfide (GSSG), also called L(−)-Glutathione.

Once oxidized, glutathione can be reduced back by glutathione reductase, using NADPH as an electron donor. The ratio of reduced glutathione to oxidized glutathione within cells is often used as a measure of cellular toxicity.

Uric Acid: It is the most important plasma antioxidant in humans, and a heterocyclic compound of carbon, nitrogen, oxygen, and hydrogen with the formula $C_5H_4N_4O_3$. It forms ions and salts known as urates and acid urates such as ammonium acid urate. Uric acid is a product of the metabolic breakdown of purine nucleotides. High blood concentrations of uric acid can lead to a type of arthritis known as gout. The chemical is associated with other medical conditions including diabetes and the formation of ammonium acid urate kidney stones.

Another aspect of this invention is the use of antioxidant enzymes to protect the longevity of HA. These enzymes can reduce the radicals and defend against ROS. They are: alpha-1-microglobulin, superoxide dismutases, catalases, lactoperoxidases, glutathione peroxidases and peroxiredoxins.

3. Anti-Hyaluronidase and Anti-Elastase

In respect to the field of cosmetic augmentation to bring back youthfulness to aging skin using cross-linked HA, an aspect of this invention uses hyaluronidase inhibitor (anti-HA) to prevent the depolymerization of HA, specifically by hyaluronidase, and to maintain the longevity of HA. Maintenance of HA longevity is important because it is directly related to the appearance of those unwanted wrinkles and the signs of aging.

HA is an important molecule to everything that lives on this earth. In that, it is a multifunctional high molecular weight polysaccharide found throughout the animal kingdom, especially in the extracellular matrix (ECM) of soft connective tissues. HA is thought to participate in many biological processes, and its level is markedly elevated during embryogenesis, cell migration, wound healing, malignant transformation, and tissue turnover. The enzymes that degrade HA, hyaluronidases (HAases) are expressed both in prokaryotes and eukaryotes. These enzymes are known to be involved in physiological and pathological processes ranging from fertilization to aging. Hyaluronidase-mediated degradation of HA increases the permeability of connective tissues and decreases the viscosity of body fluids and is also involved in bacterial pathogenesis, the spread of toxins and venoms, acrosomal reaction/ovum fertilization, and cancer progression. Furthermore, these enzymes may promote direct contact between pathogens and the host cell surfaces. Depolymerization of HA also adversely affects the role of ECM and impairs its activity as a reservoir of growth factors, cytokines and various enzymes involved in signal transduction. Inhibition of HA degradation therefore may be crucial in reducing disease progression and spread of venom/toxins and bacterial pathogens. Hyaluronidase inhibitors are potent, ubiquitous regulating agents that are involved in maintaining the balance between the anabolism and catabolism of HA. Hyaluronidase inhibitors could also serve as contraceptives and anti-tumor agents and possibly have antibacterial and anti-venom/toxin activities. Additionally, these molecules can be used as pharmacological tools to study the physiological and pathophysiological role of HA and hyaluronidases.

In one embodiment, the breast shell can have an outer layer containing at least one drug to at least minimize at least one of infection and capsular contraction. One or more biodegradable polymer layers can be dimensioned and shaped to cover the breast implant. In other embodiments, the implant may be coated with an appropriate drug-eluting coating to be described hereinafter that chemically or physically bonds to the implant and is bioabsorbable or biodegradable in the body, such that the coating dissolves over time. The drugs can elute into the surrounding tissue to inhibit, prevent or treat any bacterial infection or colonization for antimicrobial agents. Preferably, the drug is at least one antibiotic. Other drugs will also beneficially affect scarring and capsular contracture formation by interfering with collagen formation. Such other drugs include leukotriene receptor antagonists or inhibitors and/or calcium channel blockers. Other drugs may be used to treat other anticipated conditions, based on the patient and the patient's circumstances. For example, the shell containing appropriate antibiotics can provide protection against colonization by bacteria until a complete capsule can form to block the mammary ducts that blocks bacterial colonization. The layer completely surrounding the implant provides a sterile barrier around the implant that can both kill any contaminating bacteria from the surgical insertion itself as well as elute antimicrobial agents and/or other drugs after surgery to prevent bacterial migration to the implant during the healing process and to reduce and preferably eliminate capsular contracture.

Another aspect of the invention is directed to a kit comprising a breast implant with the HA of the invention. The kits are sterile. The kits optionally contain instructions for inserting the accompanying implant into the cover or for handling and surgically implanting the breast implant assembly in the subject. At the time of surgery, the kits are opened and the implant with the HA outer layer is inserted as described herein.

A further aspect is directed to a method for reducing post-surgical complications from breast augmentation or breast reconstruction in a subject which comprises surgically implanting a breast implant assembly of the invention into the subject. The breast implant assembly is used in standard surgical breast augmentation or reconstruction procedures and do not lead to any major changes or complications in those procedures.

In yet another embodiment, the HA can be used as an outer cover for sutures that inhibits a fibrotic response between the sutures and the tissue in contact with the suture material. The method includes creating a bonding matrix on a surface of the suture; exposing the surface to hyaluronic acid (HA) or polyethylene glycol (PEG); cross linking the HA or PEG; and using the suture in the body.

The resulting suture with HA layer prevents fibrin deposition through the use of HA viscous solutions. The HA barriers have the added advantage of physically preventing adjacent tissues from contacting each other and thereby reducing the probability that they will scar together. In another embodiment, inflammation is reduced by the administration of drugs such as corticosteroids and non-steroidal anti-inflammatory drugs.

Sutures used in combination with anti-scarring agents according to the present application may be useful in reducing, or reducing the risk of, excessive scarring (e.g., hypertrophic scars and keloids) and side effects resulted from excessive scarring (e.g., surgical adhesions). In certain embodiments, sutures with HA embedded on the surface themselves comprise anti-scarring agents, which are implanted into a tissue. In certain other embodiments, sutures are not first combined with anti-scarring agents, compositions comprising anti-scarring agents, or other compositions effective in reducing, or reducing the risk of, excessive scarring or associated side effects (e.g., polymer compositions). Instead, anti-scarring agents, compositions comprising anti-scarring agents, or other compositions effective in reducing excessive scarring or risk thereof (e.g., polymer compositions) are delivered separately to the site where the sutures have been, are being, or are to be implanted, to infiltrate such a site. Such delivery may be performed by the use of drug-delivery catheter or by injections or direct applications (e.g., at wound sites). Any suitable techniques by which a suture is properly implanted or used known in the art may be used. Such techniques include alpha suture, zigzag suture, coil suture, "switch back" suture, "finger-trap" suture, Connell suture, everting suture, Halsted suture, horizontal mattress suture, Lembert suture, lock or lock-stitch, locking-stitch, purse-string suture, subcuticular suture, and vertical mattress suture. Any of the aforementioned sutures may be used in combination of an anti-scarring agent. For example, sutures may be biodegradable (or absorbable) or non-biodegradable (or non-absorbable), plain or self-retaining (one-directional or bi-directional). In certain embodiments, the suture may be attached to a needle or another insertion device. In certain other embodiments, the suture may further comprise an anchor member at one end for securing the implantation of the suture in a soft or hard tissue. In certain other embodiments, the suture is a suture connector as described above. In certain embodiments, self-retaining sutures that comprise anti-scarring agents or in combination with anti-scarring agents are used. Due to their retainers, such sutures allow for joining a tissue with another tissue or with a foreign element, or repositioning a tissue without the need for using various time-consuming and skill-demanding knotting devices or techniques. In addition, the anti-scarring agents on or in the sutures or the tissues surrounding or in contact with the sutures reduce excessive scarring or the risk thereof that may cause by the retainers on the sutures.

The other methods, used for characterization of the products according to one embodiment are described in the following examples which illustrate preferred embodiments of one embodiment without, however, being a limitation thereof. Variations and modifications can, of course, be made without departing from the spirit and scope of the invention. For example, the HA can be used as facial fillers, dermal fillers, butt fillers, breast fillers, and other body part fillers. The implants of the present invention further can be instilled, before or after implantation, with indicated medicines and other chemical or diagnostic agents. Examples of such agents include, but are not limited to, antibiotics, chemotherapies, other cancer therapies, brachy-therapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

Figure 4:
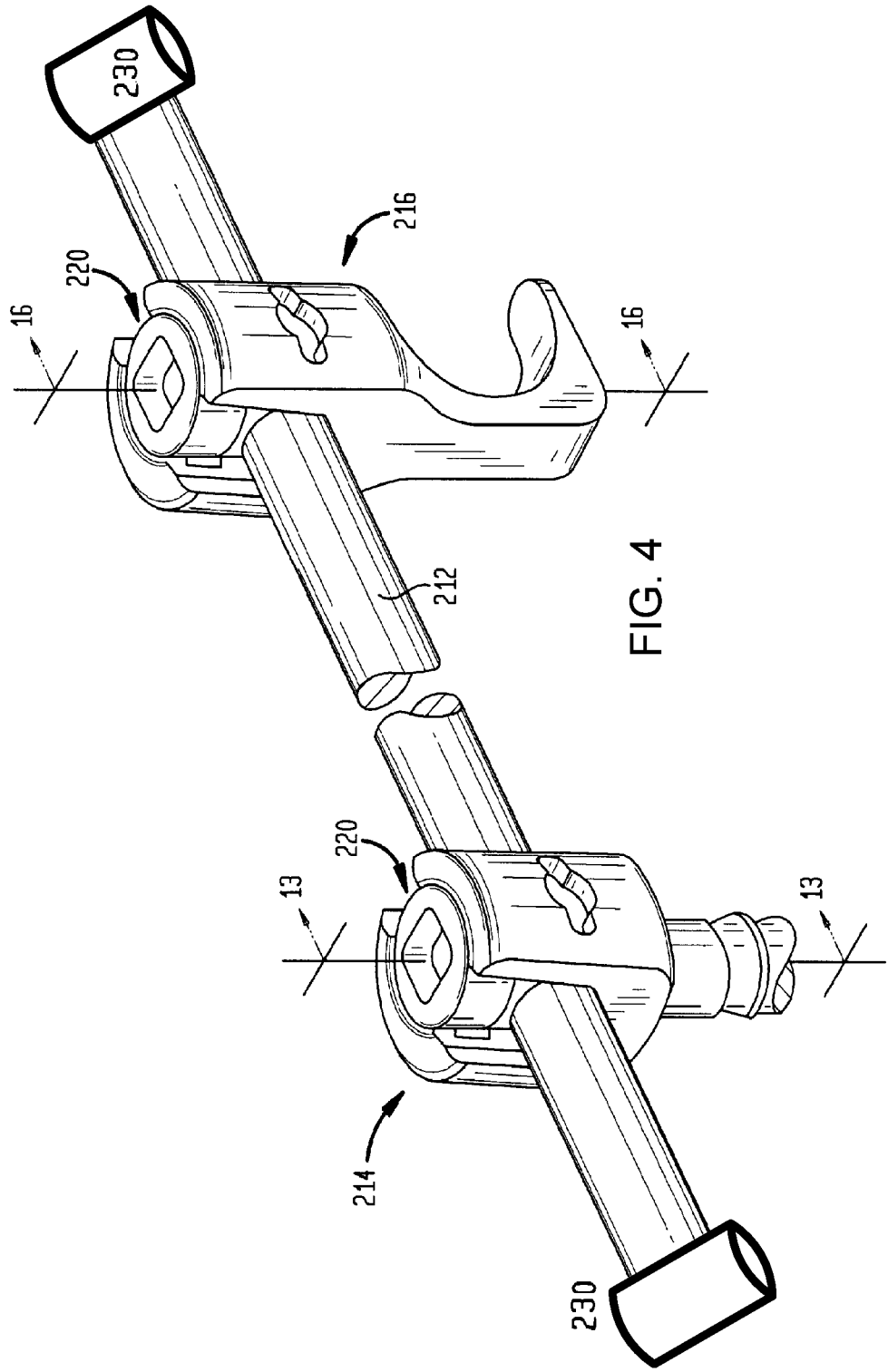
FIG. 4 shows one embodiment of an implantable rod with anti-scarring agent.
Figure 5:
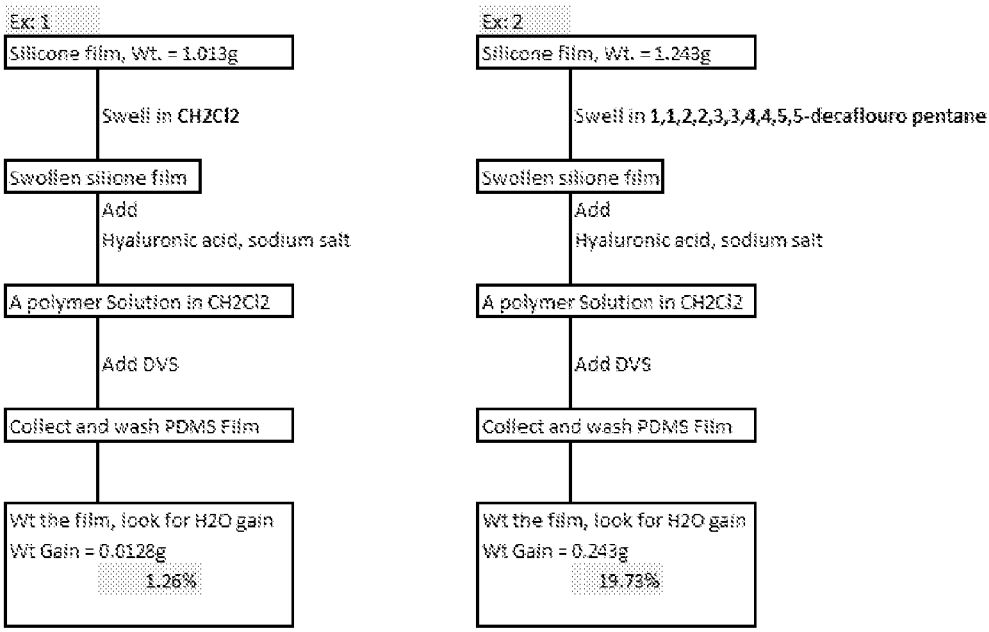
FIG. 5 shows exemplary processes to attach HA to silicon implants.
Figure 5:
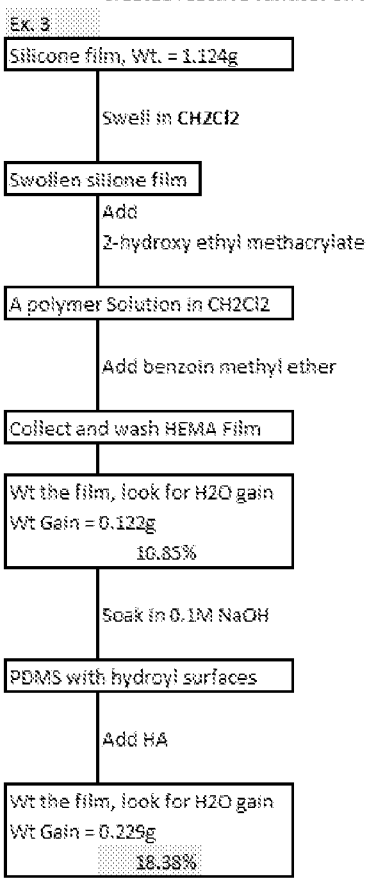

Referring now to FIG. 4, one embodiment of an implantable rod with anti-scarring agent is shown. In FIG. 4, element A includes rods 212, while element B includes screws 220 or screw/hook combination 214/216 can be used. Element C includes caps 230. To bond the HA protective layer to metal implants, the process includes applying a theta solvent to the metal prior to bonding the HA to the metal implant. In a polymer solution, a theta solvent (or θ solvent) is a solvent in which polymer coils act like ideal chains, assuming exactly their random walk coil dimensions therefore in a good solvent the Mark-Houwink equation exponent is ½. Thermodynamically, the excess chemical potential of mixing between a polymer and a theta solvent is zero.

Alternatively, the process can apply a corona treatment prior to bonding the HA to the metal implant. Many plastics, such as polyethylene and polypropylene, have chemically inert and nonporous surfaces with low surface tensions causing them to be non-receptive to bonding with printing inks, coatings, and adhesives. Although results are invisible to the naked eye, surface treating modifies surfaces to improve adhesion. Corona treatment (sometimes referred to as air plasma) is a surface modification technique that uses a low temperature corona discharge plasma to impart changes in the properties of a surface. The corona plasma is generated by the application of high voltage to sharp electrode tips which forms plasma at the ends of the sharp tips. A linear array of electrodes is often used to create a curtain of corona plasma. Materials such as plastics, cloth, or paper may be passed through the corona plasma curtain in order to change the surface energy of the material. All materials have an inherent surface energy (dyne level). Surface treatment systems are available for virtually any surface format including dimensional objects, sheets and roll goods that are handled in a web format In the embodiment of FIG. 4, a multi-axial bone screw 214 and a right-angle hook 216 are provided for securing spinal rod 212 to the spine during a spinal stabilization procedure. Both fastening devices employ a top loaded two-piece locking cap, designated generally by reference numeral 220. The two-piece locking cap increases reliability and the ease in which it is installed during a spinal stabilization procedure. While the two-piece locking cap illustrated in FIG. 3 is employed with a multi-axial bone screw, it is readily apparent that the same two-piece locking cap could be employed with a fixed axis bone screw.

The device can include a standard head portion configured to receive a customized spinal rod fabricated in accordance with the patient's body specifics, a locking cap configured to engage the head portion and the spinal rod upon rotation of the locking cap relative to the head portion to secure the position of the head portion relative to the spinal rod, and a fastener portion extending from the head portion and configured to engage the spine. The fastener portion of the device can be in the form of a screw, hook or clamp, or any other configuration known in the art.

In another form of the present invention, a biodegradable layer on a breast or buttock implant is designed to act as a switch to turn on the release of an ECM suppressing therapeutic agent (i.e. fluoroquinolone, glucosamine, diethylcarbamazine, etc.) once enough proliferation has occurred to encapsulate the implant implant or when ECM deposition begins. Exemplary fluoroquinolones include ciprofloxacin, levofloxacin, and moxifloxacin. The drug can be ciprofloxacin which is an antibiotic in a group of drugs called fluoroquinolones. In one embodiment, the Cipro can be sprayed or otherwise atomized onto the implant surface. In another embodiment, the implant can be submersed in a solution with Cipro and a binder can be provided to bind the Cipro to the implant. Ciprofloxacin fights bacteria in the body. Ciprofloxacin is used to treat different types of bacterial infections. It is also used to treat people who have been exposed to anthrax. Other medications can be used, for example, leukotriene receptor antagonists, such as zafirlukast (Accolate®), montelukast (Singulair®), and pranlukast administered orally can moderate the capsular contracture. Other medications include antibiotics surrounding the implant Finally, textured implants have yielded a reduction in capsule formation.

The method can include timing the switch to match the typical time (Encapsulation Development Time) for development of tissue encapsulation (timing approach) or to have the encapsulation event itself trigger the switch (event triggered approach).

Under the timing approach, a biodegradable layer can be coated on the therapeutic agent matrix that would degrade enough to allow therapeutic agent elution around 20 to 40 days, the typical time of tissue encapsulation of an implant implant. The layer could be configured to degrade in tissue and/or in blood. For the switch to be effective, it must effectively block ECM suppressing therapeutic agents from eluting for the duration of Encapsulation Development Time and then quickly turn on to fully elute a therapeutic agent to block proteoglycans (i.e. versican, decorin, biglycan), hyaluronan, inter-a-trypsin and/or collagen (types I and III) from being further synthesized and deposited. In this way significant ECM-related restenosis is prevented since proteoglycans and collagen are the dominant components of ECM. The ECM is responsible for the bulk of restenosis in the long term.

Since the typical ECM suppressing therapeutic agent (i.e. fluoroquinolone) is hydrophilic, a good solid barrier layer should be made of a hydrophobic or slightly hydrophobic substance to control the elution time and degradation time to better match the Encapsulation Development Time. This outer barrier layer of a more hydrophobic substance can be selected from polylactic acid (PLA), polyglycolic acid (PGA), a copolymer of PLA and PGA (PLGA), polycaprolactone (PCL), other biodegradable polyesters, polyamino acids, or other hydrophobic, biodegradable polymers.

Preferably, under the barrier layer and immediately adjacent to the therapeutic agent matrix layer another layer is provided that is instead slightly hydrophilic or closer in polarity to the therapeutic agent itself than the outer barrier layer. This middle layer is the key to the rapid, burst characteristic of therapeutic agent elution while the outer barrier layer is the key to the delayed onset characteristic of therapeutic agent elution.

As an alternative or as a complement to providing a separate layer beneath the barrier layer that is opposite in polarity to the barrier layer and closer in polarity to the therapeutic agent, the material used to form the therapeutic agent soluble material can be provided in pockets distributed throughout the barrier layer. By interspersing the barrier matrix with pockets of a hydrophilic substance (i.e. dextran, heparin) a switch effect for accelerated barrier layer degradation and therapeutic agent elution can be better achieved. Upon a threshold level of water penetration into the barrier matrix containing the pockets, the pockets increase in pressure to the point where they burst to destroy the barrier structure. The pockets act as isolated reservoirs or oases for hydrophilic physiologic and other fluids that the barrier layer's base material does not readily accept. Although the biodegradation of the barrier layer may be directed by other means such as the emergence of a restenotic environment in which the barrier layer dissolves, the incorporation of pockets allows additional options for fine-tuning the timing of barrier degradation by also making it indirectly susceptible to hydrophilic fluids and environments.

If the therapeutic agent happens to be hydrophobic rather than hydrophilic the polarities (hydrophobicity and hydrophilicity) of the respective matrices, layers, and/or pockets should be reversed. The bottom line is that the outermost barrier layer is to be opposite in polarity to the therapeutic agent and the inner layer(s) or pocket(s) that are closer to the therapeutic agent are closer in polarity to the therapeutic agent. However, preferably the therapeutic agent itself is contained in a matrix that is opposite in polarity for stabilization. The design is sandwich-like in configuration with the outer barrier and the therapeutic agent matrix analogized to pieces of bread between the unique opposite polarity inner layer or pockets analogized to the meat. The inner opposite polarity layer is the trigger to burst elution because the therapeutic agent easily desolves within it suddenly and completely.

Under the event triggered approach, there are several ways to trigger the switch to allow therapeutic agent elution to occur upon tissue encapsulation of the implant implant:

1. First, the coating covering the therapeutic agent matrix is designed to immediately break down to allow therapeutic agent elution upon tissue encapsulation. This can be achieved by coating the therapeutic agent matrix with a slightly to hydrophobic, biodegradable outer barrier layer that breaks down quickly upon the presence of a slightly to very hydrophobic environment such as provided by restenotic material. A thin layer of wax or a fatty substance exemplify the type of coating to be used. Specific examples of these include lipoprotein, collagen, polyamino acids, PLA, PLGA, and polycaprolactone, 2. Second, the ECM suppressing therapeutic agent can be bound to a molecule that inactivates the therapeutic agent until ECM factors (i.e. collagen, proteoglycans) are present.

3. Third, the switch can be turned on by other factors accompanying tissue encapsulation or extracellular matrix thickening including: hormones, enzymes, and/or peptides, etc.

4. Fourth, pressure can be used to induce release of the therapeutic agent, i.e. by housing the therapeutic agent within a semi-permeable membrane that bursts or by including pressure-building pockets within a barrier layer.

5. Fifth, pH changes can be used to induce release of the therapeutic agent if the material retaining (i.e. coating or serving as a matrix for) the therapeutic agent is sensitive to acids or bases and degrades (in tissue or in blood) upon being subjected to acidic or basic environments. In one embodiment, the therapeutic agent is coated with a slightly hydrophobic, acid-sensitive layer of PLGA. Tissue encapsulation of the implant implant can trap the PLGA and the acids produced from PLGA degradation. Subsequently, the concentration of acids is dramatically increased which leads to rapid degradation of the PLGA itself.

This event triggered approach offers a high degree of control of therapeutic agent elution and/or activation. The onset of therapeutic agent elution and/or the catalyst for therapeutic agent activation is particularized to occur independently and exclusively on the implant localities encapsulated by tissue while the elution is restrained and/or the therapeutic agent remains dormant and inactive on the implant localities that are still bare and unencapsulated. Encapsulation rates vary between procedures, individuals, and implant localities. Therefore, event-triggered therapeutic agent control provides an individualized approach for enhanced accuracy, safety and effectiveness.

It is preferred that the dosage of the anti-restenosis therapeutic agent is higher at the ends of the implant to compensate more aggressive restenosis at the ends of the implant.

In one embodiment, the present invention uses aligned nanofibers and/or aligned nanogrooves to form the implant coating to create an artificial functional endothelial layer that will attract the deposition of a natural endothelial layer. The natural endothelial layer is composed of aligned, elongated endothelial cells that will align themselves amongst the aligned fibers and deposit directly on the implant itself even when the aligned nanofiber coating is not loaded with any specifically reactive linking agents.

The xenographic/xenogenic artificial functional endothelial layer of aligned fibers and/or aligned grooves may be composed of or seeded with synthetic materials, allogeneic materials (cells or clones from a second subject of the same species as the patient), and/or heterologous materials (cells or clones from a second subject not of the same species as the patient). In any case, the aligned geometry of the artificial functional layer paves the way for the growth of a natural functional layer of autologous endothelial cells produced in vivo that will encapsulate the implant implants and injured to tissue to a depth of 0.1 mm thereby masking its xenographic (foreign) nature to preclude an immune response that may cause thrombosis.

One embodiment addresses LST without sacrificing the effectiveness of using restenosis suppressing therapeutic agents to avoid late stage restenosis and using ECM regulating therapeutic agents to reduce thickening of the ECM. This is done by depositing a biodegradable layer of aligned microfibers (AMF), aligned nanofibers (ANF), and/or aligned grooves (AG) on top of a DES as an effective means to delay the onset of release of one or more therapeutic agent (i.e. restenosis or ECM inhibitory therapeutic agents) as well as to facilitate endothelization (see FIG. 2 and FIG. 3). This way the patient benefits from two desired characteristics:

1. the safety of the BMS by having a smooth endothelium or neointima encapsulating the implant implants; and 2. the long term effectiveness of proven DES (such as Cypher and Taxus) by maintaining delivery of a local restenosis and/or ECM suppressing therapeutic agent from the implant but with a delayed onset.

The AMF/ANF/AG material may take the form of a coating, a matrix, or an implant body so long as its structure and orientation are such that it can both facilitate endothelization and also delay the onset of therapeutic agent release, if therapeutic agents are used. Preferably, the AMF/ANF/AG material lasts for 15-30 days before it is fully degraded to expose the therapeutic agent underneath. However, it may work by fully degrading anywhere between 5-60 days. The AMF/ANF/AG material is preferably made of PGA or a copolymer of PGA-PLA. These are proven compounds used on DES as well as biodegradable sutures and are well documented for their compatibility with blood. PGA and PGA-PLA are especially well suited to degrade within 15-30 days. The delay time before onset of release of the ECM suppressing therapeutic agent (i.e. fluoroquinolone, glucosamine, diethylcarbamazine, etc.) is equal to the time it takes the AMF/ANF/AG material to fully degrade. This delay time is controlled by the exact chemical compounds used to create the coating and also the coating thickness. For example, since 50% PLA:50% PGA degrades more quickly than a 75% PLA:25% PGA mix, to obtain the same therapeutic agent release onset delay a thicker layer of 50% PLA:50% PGA would be used than if a 75% PLA:25% PGA mix were used. The AMF/ANF/AG material is preferably between 0.1 micron and 20 microns thick.

Alternatively, instead of PGA and/or PLA, the AMF/ANF/AG material can also preferably be made of poly (ethylene glycol) (PEG), also known as poly(ethylene oxide) (PEO) or polyoxyethylene (POE). Caprolactone (CPL) can also be used. CPL and PEG are elastomeric materials and if the AMF/ANF/AG medical device has elastomeric properties it will better conform to the natural shape of the lumen in which it is inserted or implanted. Elastomeric materials are better able to close gaps between an implant wall and a lumen wall. Avoiding incomplete apposition of the implant implants against the lumen wall reduces the formation of stagnant pockets in which a thrombus is more likely to develop. Metallic implant implants are typically stiff and cannot conform well to the lumen when the lumen is not smooth and uniform, as is often the case. However, an elastomeric coating upon non-elastomeric implant implants ameliorates this problem by flexing, bending, expanding, and contracting to occupy the differential spaces created by the nonconformity between the lumen wall and the implant implants. Alternatively, if the implant implants themselves are made of AMF/ANF/AG elastomeric materials they can directly model the irregular surface patterns of anatomic lumens.

The AMF/ANF/AG material can also be made out of biological molecules (biomolecules) such as collagen, fibrin, or fibrinogen. Various other substances that can be used to form the AMF/ANF/AG material are: phosphorylcholine, nitric oxide, high density lipoprotein, polyzene-F, PTFE polyetherester, hydroxyapatite, polyhydroxy-butyrate, polycaprolactone, polyanhydride, poly-ortho ester, polyiminocarbonates, polyamino acids, and polyvinyl alcohol.

Irrespective of the chemical components used to form the AMF/ANF/AG material, when used as a delay coating the AMF/ANF/AG material is preferably negatively charged and also preferably has a nitric oxide functional group. Thus, as the fibers degrade, nitric oxide is released. Within the bloodstream of the lumen occupied by the implant, the nitric oxide serves to further inhibit restenosis by preventing platelet aggregation and macrophage/leukocyte infiltration, reducing smooth muscle cell proliferation, and decreasing inflammation generally while aiding the healing process. An aligned coating with a nitric oxide group (ANO) on an implant (or other intravascular medical device) forms an artificial endothelium layer due to the smooth, streamlined surface the aligned fibers/grooves provide coupled with the ability of nitric oxide to prevent aberrations on this smooth surface as the fibers degrade.

The inventor recognizes the use of any biocompatible materials that can be formed into aligned nanofibers, aligned microfibers, or aligned grooves for the AMF/ANF/AG material used to form an implant, a coating, or a matrix for therapeutic agent(s). The present invention also recognizes the ability to use the AMF/ANF/AG material in conjunction with other coatings, layers, matrices, pores, channels, reservoirs, etc. to delay onset of the release of any therapeutic agent and/or to encourage structured (i.e. aligned) endothelization.

The present invention also teaches the criticality of matching the time period of delay prior to therapeutic agent release with the time it takes for the AMF/ANF/AG implant surface to become covered (i.e. encapsulated) by endothelization to a depth of approximately 0.1 mm. The artificial functional endothelium layer itself is a very thin (i.e. only one or a few cells thick). A thin layer does not burden the implant with unnecessary volume (i.e. on the periphery of a cross-section) that could make insertion and adjustment within the lumen more difficult. A thin layer also does not significantly reduce the inner diameter of the implant's lumen and therefore does not interfere with hemodynamics or obstruct blood supply to a treated area.

When the implant is not formed of a material (i.e. such as an elastomeric aligned material) that enables it to conform to the shape of a lumen surface, a thrombus is more likely to develop causing a localized inflammatory reaction. Also, when the implant doesn't conform well to the shape of a lumen, the process of restenosis cannot be effectively controlled. Although systematic therapeutic agents administered with BMS and therapeutic agents supplied by DES can slow or modulate the rate of ineffective restenosis they are not typically used to encourage a moderate amount of beneficial restenosis. Any restenosis that does occur in a vessel having an uneven surface with implant implants that inadequately conform to the natural cell and protein structure (and/or shape) of the vessel is likely to be uncontrollable and problematic. Smooth muscle cell migration and proliferation is likely to form the first tissue layer over the implant implants. In contrast, the present invention provides a preformed artificial functional endothelial layer to provoke a first in vivo layer of natural endothelial cell growth.

According to the present invention, an aligned (i.e. AMF/ANF/AG/ANO) coating on the luminal surface aligns both the blood flow and the growth of natural endothelial cell layers in a uniform, optimal direction (i.e. longitudinally along the central axis of the lumen). An aligned inner coating accelerates and optimizes blood flow for better drainage and support. Normal blood flow around the implant flushes out immune response agents and toxins, as they are produced, to accelerate drainage and healing. Normal blood flow also feeds the developing, natural endothelial cell layer above the artificial functional endothelial implant coating with nutrients.

Once the natural endothelial cell layer has developed to a sufficient extent (i.e. a depth of approximately 0.1 mm) and moderate amounts of beneficial (i.e. aligned) restenosis have been permitted to occur, the result is a camouflaged implant buried within normal, healthy tissue. No foreign materials are detectable by the blood and so the blood related immune response and inflammation are inhibited, thereby greatly reducing the risk of thrombosis. As therapeutic agents begin to be eluted from DES upon degradation of the aligned coating, the beneficial, controlled restenosis process ("encapsulation") comes to a halt. The implant remains stably buried but the thickness of the luminal walls stops increasing to avoid reclosure. The therapeutic agents are powerful enough to prevent additional encapsulation but cannot undo the beneficial, implant-sealing, encapsulation that has already occurred.

Elution of the therapeutic ECM suppressing therapeutic agent will arrest the proliferation of neointima (protein deposition) (see FIG. 4). Due to the delay in the onset of therapeutic agent release, by the time the therapeutic agents are released all the implant implants are encapsulated with endothelium and/or smooth muscle. Therefore, higher dosages of therapeutic agents, faster elution rates, and/or more aggressive therapeutic agents can be used to ensure maximum effectiveness in preventing restenosis and inhibiting excessive ECM thickening in the long term without fear of LST from an immune reaction. Once the implant implants are smoothly buried beneath a thin natural tissue layer thrombosis is unlikely.

Optionally, the implant may have semi-permeable cross-sectional side walls extending through the surface area of the cross section on each end adjacent to a target site to be treated with an eluted therapeutic agent. The side walls would serve as barriers to the therapeutic agent to concentrate it at the target site and avoid the negative effects of systematic therapeutic agent distribution. Such sidewalls would also conserve the therapeutic agent to be maintained where it is needed most to allow less total therapeutic agent within the implant to be equally effective by reducing the washout effect. Reducing the total therapeutic agent stored in the state (while maintaining effectiveness) is beneficial because then the implant walls can be thinner and it is also less expensive. The semi-permeable nature of the side walls allows them to permit the influx of important nutrients needed at the constricted vessel site and to permit the outflux of waste thus preserving hemodynamics. The cross-sectional side walls would dissolve naturally in time to correspond with the termination of the desired therapeutic agent treatment period.

Optionally, the implant may include radio-opaque substances in one or more of the materials of which it is formed or in one or more coatings. An array of different, distinguishable radio-opaque substances may also be used in each layer or coating. These substances would enable a physician to externally observe the placement, progress, and improvement of the implanting procedure without causing the patient discomfort from an internal inspection and without risking displacing the implant during an internal (i.e. endoscopic) inspection.

Another approach to avoiding LST while still controlling restenosis is by accelerating the endothelization of the implant through aligned scaffolding without the antirestenosis therapeutic agent. The bare implant can be made of (at least in part) or coated with elongated AMF/ANF/AG/ANO aligned with the direction of blood flow (i.e. long axis of fibers parallel to the direction of blood flow). Endothelial cells (ECs) are themselves elongated and tend to also be aligned with the direction of blood flow. By aligning the fibers with the preferred alignment of ECs, the deposition of ECs over the implant (including but not limited to the implant implants) is accelerated (aligned scaffolding). The presence of ECs tends to arrest the restenosis process (smooth muscle proliferation). The AMF/ANF/AG/ANO are preferably laid down on the inner diameter (ID) of the implant (see FIG. 3). The outer diameter (OD) or abluminal surface of the implant is typically embedded in or aligned against the luminal surface of the vessel so that the longitudinal alignment of the fibers here is not as important as for the inner diameter or luminal surface of the implant.

The implant implants are typically 50 to 100 microns wide. The fibers are preferably 0.5 to 10 microns wide. Therefore, regardless of the implant implant orientation, the fibers can have an aspect ratio of 5 or greater. By having an aspect ratio greater than 2, the fibers can provide effective longitudinally aligned scaffolding for ECs to grow on.

The AMF/ANF/AG/ANO coating or surface can be impregnated or coated with antiplatelet or anticoagulant therapeutic agents such as heparin, ticlopidine, chlopidrel, enoxaparin, dalteparin, hirudin, dextran, bivalirudin, argatroban, danparoid, Tissue Factor Pathway Inhibitor (TFPI), GPVI antagonists, antagonists to the platelet adhesion receptor (GP1b-V-IX), antagonists to the platelet aggregation receptor (GPIIb-IIIa) or any combination of the aforementioned agents.

The AMF/ANF/AG/ANO material can also be impregnated with endothelization promoting substances such as vascular endothelial growth factor (VEGF), angiopoietin-1, antibodies to CD34 receptors, and/or hirudin, dextran.

The coating can be applied to the inner diameter (ID) of the implant in the form of longitudinally aligned microfibers, nanofibers, grooves, or nitric oxide carrying elements by several modified processes of electrospinning:

1A. Aligned Nanofibers on implant implants only: A dispensing syringe is loaded with a solution of the fiber material and is charged (i.e. positive) with a high voltage (>1 kV) to charge the solution. The implant is either grounded or charged by applying the opposite voltage (i.e. negative). The outer diameter (OD) of the implant is covered with a polar or conductive tube that sticks to the fiber material well. For example, if PGA or PLA are used as the polymer solution from which the fiber material is formed, polyethylene terephthalate (PET) is heat shrunk on the OD of the implant. The implant is held by a grounded or charged (i.e. negative) collet on the OD of one end. The dispensing syringe needle with a 90 degrees bend (or side hole) at the tip is inserted inside the ID of the implant from the open end of the implant. The charged solution is dispensed from the needle tip onto the implant ID as longitudinally aligned micro/nanofibers/grooves/nitric-oxide carrying elements as the syringe tip is moved back and forth longitudinally. As the syringe tip completes one pass from one end to the other, the collet is indexed (turned incrementally) to lay down the adjacent fiber. This process continues until the whole implant ID is covered with aligned fibers, grooves or elements. Once the coating is finished, the cover (i.e. polar or conductive tube such as PET) on the OD can be peeled off to clear the implant openings of fibers.

1B. Aligned Nanofibers covering all implant: A dispensing syringe is loaded with a solution of the fiber material and is charged (i.e. positive) with a high voltage (>1 kV) to charge the solution. The implant is either grounded or charged by applying the opposite voltage (i.e. negative). The implant is held by a grounded or charged (i.e. negative) collet on the OD of one end. The dispensing syringe needle with a 90 degrees bend (or side hole) at the tip is inserted inside the ID of the implant from the open end of the implant. The charged solution is dispensed from the needle tip onto the implant ID as longitudinally aligned micro/nanofibers/grooves/nitric-oxide carrying elements as the syringe tip is moved back and forth longitudinally. As the syringe tip completes one pass from one end to the other, the collet is indexed (turned incrementally) to lay down the adjacent fiber. This process continues until the whole implant ID is covered with aligned fibers, grooves or elements.

2. The highly charged (i.e. +10 kV) syringe as described above is fixed longitudinally. The implant is grounded. A ring of opposite charge (i.e. −10 kV) is placed near the implant. The dispensing syringe is pulsed by pulsing syringe pressure, a needle valve, or charging to completely dispense one aligned fiber. The implant is then rotationally indexed for the next pulsed dispensing.

3. A hollow ring containing the solution of fiber material has series of micro/nano-holes on the end for dispensing parallel fibers arranged in a diameter close to the diameter of the implant. The ring is highly charged (i.e. +10 kV) to charge the fiber material in solution. The implant is grounded. A ring close to the diameter of the implant is charged with an opposite charge (i.e. −10 kV) on the opposite end of the implant. This charged state will cause the solution which forms the fibers to eject from the holes in parallel, longitudinally towards the oppositely charged ring while simultaneously adhering to the implant along the path from one ring to another.

In another embodiment, the inner surface of the implant implant can have micro/nano-grooves etched on it longitudinally (parallel to axis of implant). ECs will tend to grow into these grooves. The grooves are preferably 1 to 10 microns wide. In the same manner, the grooves can also be ridges or channels. The longitudinally aligned micro/nano-grooves may also be used as reservoirs or longitudinal wells for storing therapeutic agents within the aligned fiber layers for controlled or multi-phase elution.

These AMF/ANF/AG/ANO implants are particularly advantageous when applied to intravascular bifurcations or vessels with one or more corollary branch adjacent to a main lumen. Bifurcated vessels tend to have much higher rates of restenosis with both conventional BMS and DES than do non-bifurcated vessels.

The present invention controls tissue encapsulation of the implant and of injured tissue in at least three ways: biologically, geometrically, and chronologically.

Biologically, aligned nano/microfibers with or without aligned nano/microgrooves therein (or alternatively, aligned grooves formed within a non-fibrous material) facilitate functional endothelization by encouraging a uniform orientation in any cell growth that occurs (whether of true endothelial cells or artificial endothelial cells). The polymers or other materials chosen for the construction of the nano/microfibers or nano/microgrooves must be biocompatible to permit the natural flow of blood and other bodily fluids through the lumen adjacent the implant's inner surface without elicitation of an immune response or thrombosis. The materials used to form the fibers or the material within which the grooves are etched can be synthetic or naturally derived. Suitable materials include: biodegradable materials such as polyglycolic acid (PGA), polylactic acid (PLA), copolymer of PLA and PGA (PLGA), hydroxyapatite (HA), polyetherester, polyhydroxybutyrate, polyvalerate, polycaprolactone, polyanhydride, poly-ortho ester, polyiminocarbonates, polyamino acids, polyethylene glycol, polyethylene oxide, and polyvinyl alcohol; non biodegradable polymers such as fluoropolymer like Polytetrafluoroethylene (PTFE), polyzene-F, polycarbonate, carbon fiber, nylon, polyimide, Polyether ether ketone, polymethylmethacrylate, polybutylmethacrylate, polyethylene, polyolefin, silicone, and polyester; biological substances such as high density lipoprotein, collagen, fibrin, phosphorylcholine (PC), gelatin, dextran, or fibrinogen.

Geometrically, the invention is designed to only allow 0.1 mm thickness of encapsulation (of implant implants or the entire implant body and of injured tissue) before the therapeutic agent elution process begins to inhibit further encapsulation. Another aspect of geometric control is the alignment of fibers/grooves and all growth thereupon whether it be endothelial cells, smooth muscle cells, proteins, matrix fibers, or collagen fibers. Due to the structure supplied by the fibers/grooves, all subsequent in vivo growth, migration, and/or proliferation is necessarily aligned to correspond to the template set by the fibers/grooves. Aligned growth does not interfere with blood flow. Further, even if the initial natural layers of biologically derived materials deposited are not the ideal materials (i.e. smooth muscle cells instead of endothelial cells), as long as they are aligned they are suspected not to impede the deposition of the optimal materials when they come along.

Chronologically, the invention assures that the complete degradation of the polymer (or other material) layer serving as a delay coat for the antiproliferative therapeutic agent corresponds to the time when an optimal amount (i.e. 0.1 mm thickness) of encapsulation has occurred because that point in time also marks the onset of elution of the antiproliferative therapeutic agent which will suppress further thickening of tissue encapsulation. Temporal control over the elution of the antiproliferative and/or other therapeutic agents may also be achieved by an external activation means that signals for the aligned therapeutic agent reservoirs to begin elution. The external activation means may be electromagnetic radiation, infrared light, microwave radiation, x-ray radiation, etc. This type of external activation means would provide very precise control of the onset of therapeutic agent elution. Since the rate of encapsulation will vary from individual to individual and from procedure to procedure depending upon a multitude of factors, a pre-elution assessment (i.e. imaging for endothelial cell markers) of the extent of encapsulation can precede initiation of the external activation means to ensure elution does not begin prematurely.

In some embodiments, the teachings are directed to a therapeutic coating that promotes formation of a functional endothelium on a medical device. In these embodiments, the coating comprises a biodegradable drug-containing layer that is positioned over a surface of a medical device and serves as a source of a drug that functions as an antiproliferative agent in a subject. The coating also comprises a biodegradable drug-reservoir layer positioned over a surface of the drug-containing layer. The drug-reservoir layer comprises a drug-retaining layer, wherein the drug-retaining layer is void or substantially void of the drug at a time of implantation in the subject and functions to retain and at least substantially block an initial release of the drug into the subject for a time sufficient to form a functional endothelium over the surface of the medical device. In these embodiments, the functional endothelium can provide a source of thrombomodulin to the subject. It should be appreciated that the drug may be at least substantially miscible in the drug-reservoir layer to facilitate a retention of the drug. It should be appreciated that the time sufficient to form a functional endothelium may vary according to selection of subject, medical device, location of an implant, materials used, and the like. In some embodiments, the time can be at least about 20 days.

In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons. And, in some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

Moreover, the drug-retaining layer can comprise a polymer having ester-terminal groups. The polymer can have, for example, a molecular weight ranging from about 50 KDaltons to about 190 KDaltons, and a structure that remains at least substantially undegraded during the initial release of the drug, the structure comprising P—CO2R, where P is the polymer backbone and R is an alkyl group having from 1 to 4 carbons.

The coating may at least substantially promote development of the functional endothelium as the source of the thrombomodulin when compared to a control development of such endothelium formation observed following implantation of a metal or polymer drug-eluting medical device. In addition, the coating may at least substantially inhibit development of a hyperproliferative tissue when compared to a control development of such hyperproliferative tissue observed following implantation of a metal or polymer medical device that does not elute a drug. In some embodiments, the medical device comprises an implant.

The coatings can be designed for a delay time before onset of the release of the drug and elution of the drug at a certain rate. In some embodiments, the drug-reservoir layer can further comprise an accelerant layer to accelerate the onset of elution. And, in some embodiments, the accelerant layer having a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons. In some embodiments, the accelerant layer can comprise a drug. The amount of drug in the accelerant layer can be 0, 5, 10, 15, 20, 25, 30, 35, 40, 45, 50, 60 percent, or any amount therein.

In fact, other variables can be used to design for a desired delay time and release rate of the drug. In some embodiments, for example, the thickness ratio of the drug-reservoir layer to the drug-containing layer can range from about 4:1 to about 10:1, and the miscibility of the drug in a coating can be preselected to affect the rate of drug migration. In some embodiments, the thickness of the coating can range from about 2 microns to about 9 microns. And, in some embodiments, the thickness ratio of the drug-retaining layer to the drug-containing layer ranges from about 4:1 to about 7:1.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. In some embodiments, the drug-reservoir layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-reservoir layer, is more hydrophilic than the remainder of the drug-reservoir layer, and comprises at least one sub-layer having a thickness of less than or equal to 3 microns, where a repeated application of the sub-layer is used to form thicknesses of greater than 3 microns. The application of the sub-layers can be used to at least substantially promote a retention of the drug in the drug-containing layer during formation of the coating when compared to such a coating without the application of the sub-layers.

The coatings taught herein can, in some embodiments, further comprise pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, estradiol, and transcription factor E2F1.

In some embodiments, the teachings are directed to a medical device having a drug-retaining coating that at least substantially delays the initial elution of a drug for a time effective at forming a functional endothelium over a surface of the medical device. In some embodiments, the coatings are a switch for "turning on" drug elution at a desired time, where the switch can be programmed through coating design to elute at the desired time using the methods taught herein. In some embodiments, the coating can be designed to elute at a desired rate after the onset of elution.

Merely forming an endothelium is not the same as forming a functional endothelium. The term "functional endothelium" includes, for example, an endothelium that functions to at least provide a localized source of thrombomodulin, nitric oxide, or a combination thereof. On a functional endothelium, for example, there is typically an abundance of thrombomodulin, a protein that inhibits blood clot formation. Besides the benefits of thrombomodulin in reducing blood clots, there are several other benefits of a functional endothelium. A functional endothelium, for example, can also inhibit hyperproliferative tissue growth long term or produce nitric oxide that can allow the blood vessels to dilate to accommodate increased blood flow from exercise for example.

In some embodiments, a coating "at least substantially delays the initial elution" includes, for example, where there is no measurable elution of drug for an initial period of time, or the elution of drug over the initial period of time is negligible or sufficiently retained, such that the desired effect that would be obtained in the absence of any drug elution is still obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. And, "a time effective at forming a functional endothelium over a surface of the medical device" can be, for example, any duration of time in which the elution of drug can be entirely or partially inhibited to allow for formation of an endothelium that provides a localized source of thrombomodulin where desired, in an area of an implant. In some embodiments, the terms "block", "delay", and "retain" can be used interchangeably.

The coating can comprise a drug-containing layer applied over a surface of the medical device. In some embodiments, the drug-containing layer can be 100% drug. In some embodiments, the drug-containing layer can comprise 5, 10, 15, 20, 25, 30, 35, 40, 45, 50, 55, 60, 65, 70, 75, 80, 85, 90, 95, 99, 100 percent drug, or any amount therein.

The surface of the medical device can include any surface of a medical device, such as an implanted medical device.

The surface may be, for example, a breast or buttock implant, in some embodiments. The drug-containing layer can be used to provide a drug that functions as an anti-proliferative agent; and, a drug-reservoir layer can be applied over the drug-containing coating.

In some embodiments, the drug reservoir layer can comprise a drug-retaining layer that is void or substantially void of the drug at a time of implantation in a subject. A layer can be considered "substantially void" of the drug where the layer has an almost immeasurable amount of drug in the layer, or the amount is so small that the effect on the delay in onset of drug elution is still controllable using the coatings and methods taught herein. In some embodiments, a layer is substantially void of the drug, where the amount of drug is negligible or sufficiently small, such that the desired effect of the delay in the onset of elution would be obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. In some embodiments, a layer is substantially void of drug where the drug composes less than 2.0, 1.0, 0.8, 0.6, 0.5, 0.4, 0.3, 0.2, 0.1, 0.09, 0.08, 0.07, 0.05, 0.03, 0.01, 0.001 percent of the layer, or any amount therein.

And, in some embodiments, the coating can at least substantially promote development of a functional endothelium, the functional endothelium providing an additional a source of thrombomodulin when compared to a control development of an endothelium formation observed following implantation of a metal or polymer drug-eluting medical device. Moreover, in some embodiments, the coating can at least substantially inhibit development of a hyperproliferative tissue when compared to a control development of such hyperproliferative tissue observed following implantation of a metal or polymer medical device that does not elute a drug. As such, the teachings are also directed to a method of inhibiting the formation of hyperproliferative tissue and promoting the formation of a functional endothelium after implantation of a medical device in a subject. Moreover, the teachings also provide a method of obtaining one of the devices taught herein and implanting the device in a subject.

The teachings are naturally directed to include a therapeutic coating that promotes formation of a functional endothelium on a medical device. The coating comprises a biodegradable drug-containing layer that is positioned over a surface of a medical device and serves as a source of a drug that functions as an anti-proliferative agent in a subject. The coating can also comprise a biodegradable drug-reservoir layer positioned over a surface of the drug-containing layer. The drug-reservoir layer can comprise a drug-retaining layer, wherein the drug-retaining layer can be void or substantially void of the drug at a time of implantation in the subject and function to retain and at least substantially block an initial release of the drug into the subject for a time sufficient to form a functional endothelium over the surface of the medical device. As discussed, the functional endothelium can provide a beneficial source of thrombomodulin to the subject to an area affected by a medical device.

It should be appreciated that, in the embodiments taught herein, the drug may be selected by its miscibility in a preselected polymer matrix. For example, the drug may be selected because it is at least substantially miscible in the drug-reservoir layer in order to retain the drug for a desired amount of time. Or, the drug may be miscible to a preselected degree, an amount sufficient to facilitate a desired retention time of the drug. A desired retention time is facilitated, for example, in a case where a functional endothelium has formed to a desired extent. It should be appreciated that the desired retention time is facilitated where the retention time is modulated to a desired amount, and the modulation of the time can include an increase or a decrease in the retention time through altering one or more coating variables, as described herein. One of skill should appreciate, for example, that miscibility of the drug with the polymer is a variable that can modulate an affinity of the drug for the polymer, in some embodiments, thus affecting retention time.

In some embodiments, the drug and polymer are mixed or blended in solution, and one skill will appreciate that the mixes or blends can be considered substantially miscible, for example, where they mix or blend homogeneously in the desired proportions of drug to polymer, at least for the purposes of the teachings provided herein. In contrast, the mixes or blends may be considered immiscible, at least for the purposes of the teachings provided herein, where the mix or blend of polymer and drug is not homogeneous in the mix or blend in the proportions desired. In some embodiments, a drug can be considered substantially miscible in a polymer, where a homogeneous, saturated solution comprising the drug in a solvent spreads on a layer of the polymer, such that (i) the solution of the drug in the solvent has a contact angle of greater than 90 degrees on the surface of the polymer; and (ii) the layer of the polymer was formed used the same solvent. In some embodiments, the drug is substantially miscible in the polymer where the surface tension of the drug and the surface tension of the polymer are the same or similar when compared using the same solvent. A surface tension is the same, where the difference is not statistically significant, and similar, where the surface tension does not vary by more than 1, 2, 3, 4, 5, 10, 15, 20, 25, or 30 percent, in some embodiments. It should be appreciated, however, that any method known to one of skill can be used to determine the relative degree of miscibility and affinity between the drug and the polymer.

In some embodiments, the retention time of a drug can be a time sufficient amount, or an otherwise desired amount of time, chosen based on any number of parameters recognized and known to one of skill in the art of drug elution from implanted medical devices. Such parameters can vary the desired amount of time based on, for example, type of implant, location of implant, construction of implant, selection of drug, desired effect, and the like.

It should be appreciated that the "time sufficient to form a functional endothelium" may vary according to selection of subject, medical device, location of an implant, materials used, and the like. In some embodiments, the time can be at least about 20 days. In some embodiments, a sufficient amount of time can range from about 5 days to about 120 days, from about 10 days to about 90 days, from about 12 days to about 50 days, from about 14 days to about 45 days, from about 15 days to about 90 days, from about 20 days to about 60 days from about 25 days to about 45 days, from about 20 days to about 40 days, from about 20 days to about 30 days, from about 25 days to about 35 days, or any range therein.

The polymeric compositions taught herein include any desired polymer, combination of polymers, copolymers and agents known to one of skill to be useful as a medical device, or coating, as taught herein. These polymers can be biodegradable due to their labile nature, such as the labile nature of the ester groups that are present in some polymers. In some embodiments, these compositions can be designed such that they can be broken down, absorbed, resorbed and eliminated by a mammal. As such, the compositions can be used, for example, to form medical articles and coatings.

The terms "combine," "combined," and "combining" all refer to a relationship between components of a composition and include blends, mixtures, linkages, and combinations thereof, of components that form the compositions. The linkages can be connections that are physical, chemical, or a combination thereof. Examples of physical connections include, but are not limited to, an interlinking of components that can occur, for example, in interpenetrating networks and chain entanglement. Examples of chemical connections include, but are not limited to, covalent and noncovalent bonds. Covalent bonds include, but are not limited to, simple covalent bonds and coordinate bonds. Non-covalent bonds include, but are not limited to, ionic bonds, and intermolecular attractions such as, for example, hydrogen bonds and attractions created by induced and permanent dipole-dipole interactions.

Compositions that are selected for an in vivo use should meet particular requirements with regard to physical, mechanical, chemical, and biological properties of the compositions. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing. An example of a chemical property that can affect performance of a biodegradable composition in vivo is the rate of absorption of the composition by a subject. An example of a biological property that can affect performance of a composition in vivo is the bioactive and/or biobeneficial nature of the composition, While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo, such as for the release of a drug. In some embodiments, an increase in hydrolysis can also increase the release rate of an agent by creating channels within a medical article or coating that can serve as transport pathways for diffusion of the agents from the composition. The terms "subject" and "patient" can be used interchangeably and refer to an animal such as a mammal including, but not limited to, non-primates such as, for example, a cow, pig, horse, cat, dog, rat, and mouse; and primates such as, for example, a monkey, or a human.

In some embodiments, the compositions may be used, for example, to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and absorption rate; and (iv) that can be combined with agents that are not only bioactive and/or biobeneficial but also control a physical property and/or a mechanical property of a medical article or coating formed from the polymer.

A polymer or coating can be "biodegradable," for example, when it is capable of being completely or substantially degraded or eroded when exposed to an in vivo environment or a representative in vitro environment. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application. The polymers used in the teachings herein may be biodegradable and may include, but are not limited to, condensation copolymers. In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons.

Biodegradable polymers can be used, and biodegradable polymers should be selected according to their behavior and hydrolysis in vivo. In some embodiments, the number average molecular weight of the polymer fragments should be at or below about 40,000 Daltons, or any range therein. In some embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

Examples of polymers that can be used in some embodiments include, but are not limited to, poly(acrylates) such as poly(butyl methacrylate), poly(ethyl methacrylate), poly(hydroxylethyl methacrylate), poly(ethyl methacrylate-co-butyl methacrylate), copolymers of ethylene-methyl methacrylate; poly(2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); poly(propylene) co-poly(ether-esters) such as, for example, poly(dioxanone) and poly(ethylene oxide)/poly(lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly(ethylene glycol) and poly(propylene glycol);

epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, other polymers may be selected such that they specifically exclude any one or any combination of these polymers.

In some embodiments, the coatings can comprise one or more biodegradable polymers. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, poly(ester amides); amino acids; PEG and/or alcohol groups, polycaprolactones, poly(L-lactide), poly(D,L-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), poly-alkylene oxalates, polyphosphazenes, PHA-PEG, and any derivatives, analogs, homologues, salts, copolymers and combinations thereof. In some embodiments, the polymers can include poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of these polymers.

In some embodiments, the polymers can be chemically connected by covalent bonds. In some embodiments, the polymers can be chemically connected to by non-covalent bonds such as, for example, by ionic bonds, inter-molecular attractions, or a combination thereof. In some embodiments, the polymers can be physically connected. In some embodiments, the polymers can be chemically and physically connected. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed.

The behavior of the polymer matrix can be changed through selection of any number of factors that provide the desired drug elution, chemical and physical characteristics of the coatings taught herein. For example, the terminal end groups can be designed to contribute to imparting such characteristics in the polymers. A more hydrophilic end-group can increase the rate of ingress of water, for example, and likewise increase the rate of hydrolysis of the polymer chains, at least in some embodiments. Likewise, a less hydrophilic group can deter in the ingress of water, and slow the rate of hydrolysis, at least in some embodiments.

It should be appreciated that a polymer can be selected to have acid terminal end-groups, hydroxyl terminal end-groups, alkyl-ester end-groups, or a combination thereof. Moreover, a polymer layer can be created using sub-layers, where the layer can have a sub-layer having acid groups, a sub-layer having hydroxyl groups, a sub-layer having ester end-groups, or a combination thereof. In fact, the construction of the layers and sub-layers can be designed based on thickness ratios to design a coating that provides a desired characteristic or set of characteristics including, but not limited to, drug-retention time, a desired rate of hydrolysis, a desired glass transition temperature, a desired drug-elution rate, a desired toughness, a desired elasticity, a desired modulus, or a combination thereof.

Molecular weights can also be selected for the polymer in a particular layer or set of layers in the coating, as a mixture of molecular weights in a particular layer or set of layers, or as a set of sub-layers, where each layer in the sub-layer can have an independently selected molecular weight, mixture of molecular weights, or a combination thereof, where the molecular weight or mixture of molecular weights can be the same or different for each sub-layer. And, in many embodiments, a desired characteristic is that the polymers have a structure that remains at least substantially undegraded during the initial release of the drug. In some embodiments, for example, the drug-retaining layer can comprise a polymer having ester-terminal groups.

In some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

The molecular weights can be selected and tailored for a particular polymer selection and for a particular coating layer and purpose. For example, the polymer can have a molecular weight ranging from about 50 KDaltons to about 190 KDaltons, from about 50 KDaltons to about 190 KDaltons, from about 50 KDaltons to about 180 KDaltons, from about 60 KDaltons to about 170 KDaltons, from about 70 KDaltons to about 160 KDaltons, from about 80 KDaltons to about 150 KDaltons, from about 90 KDaltons to about 140 KDaltons, from about 90 KDaltons to about 160 KDaltons, from about 100 KDaltons to about 160 KDaltons, or any range therein.

Without intending to be bound by any theory or mechanism of action, in some embodiments, the drug-reservoir layer is initially implanted in a "drug-absorbing" state and is later transformed into a "drug-release" state over time due to changes in the physical and chemical structure across the coating in vivo. In the drug-absorbing state, the drug-reservoir layer has the highest affinity for the drug. In the drug-release state the drug-reservoir layer has a substantially lower affinity for the drug. The drug can have the highest solubility in the drug-reservoir layer in the drug-absorbing state and in the drug-release state, the drug can have a substantially lower solubility in the drug-reservoir layer. In some embodiments, the drug-absorbing state can reflect the state in which the glass transition temperature (Tg) of the drug-reservoir layer is higher than the temperature of the surrounding tissue/fluid, and the drug-release state can reflect the state at which the Tg of drug-reservoir layer is equal to or less than that of surrounding tissue/fluid. In some embodiments, coating has a Tg above the surrounding tissue temperature of 37 degrees C.

The polymer end-groups can have any structure known to one of skill that will provide the desired polymer characteristics for a particular coating layer or set of layers. In some embodiments, the end-group can be an ester-terminal group. For example, the polymer structure can comprise P—CO2R, where P is the polymer backbone and R can be an alkyl group having from 1 to 4 carbons, from 1 to 20 carbons, from 2 to 12 carbons, from 1 to 10, from 2 to 8, from 1 to 6 carbons, from 1 to 5 carbons, or any range therein. In some embodiments, R can be any end-group known to one of skill, with the limitation that R cannot affect usefulness of the polymer, for example, the ability of the polymer to be applied as a coating on a desired medical device. In some embodiments, R can be saturated, unsaturated, aromatic, aliphatic, or any combination thereof.

In some embodiments, an R group can be a H; an aliphatic hydrocarbon group such as, for example, an alkyl, alkenyl, or alkynyl group; an aromatic group such as, for example, an aryl, aralkyl, aralkenyl, of aralkynyl group; various other groups as defined herein, or a combination thereof.

In some embodiments, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 4 to about 200 carbon atoms, from about 6 to about 150 carbon atoms, from about 12 to about 120 carbon atoms, from about 18 to about 90 carbon atoms, from about 24 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, isooctyl, nonyl, decyl, and the like; lower alkylene such as, for example, ethylene, propylene, propylene, butylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain including at least one alkene functionality. The term "alkynyl" refers to a straight-chained or branched carbon-containing chain including at least one alkyne functionality. The term "aryl" refers to a carbon-containing ring bearing a system of conjugated double bonds often comprising at least six π (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of side chains having 1 or more carbon atoms. In some embodiments, a radical is straight-chained if it has less than 0.01 mole percent of such side chains. In some embodiments, a radical is straight-chained if it has less than 0.001 mole percent of such side chains. A radical is "branched" when it has more than 0.1 mole percent of side chains having 1 or more carbon atoms. In some embodiments, a radical is branched when it has more than 0.01 mole percent of such side chains. In some embodiments, a radical is branched when it has more than 0.001 mole percent of such side chains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted. Examples of substituents in substituted radicals include, but are not limited to, hydroxyls, alkyls, carboxyls, esters, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

In some embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In some embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In some embodiments, the functional groups can be oxygen-containing groups including, but not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In some embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In some embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In some embodiments, the functional groups can include, but are not limited to, sulfur-containing groups such as sulfones, sulfides, sulfinamides, sulfilimines, sulfimides, sulfinamides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides, sulphur diimides, thio, thioacetals, thioaldehydes, thioanhydrides, thiocarboxylic acids, thiocyanates, thioether, thiohemiacetals, thioketones, thiol, thiolates, xanthic acids, and combinations thereof.

In some embodiments, the functional groups can include, but are not limited to, silyl groups, halogens, selenoethers, trifluoromethyls, thio-derivatives of urethanes where at least one oxygen atom is replaced by a sulfur atom, phosphoryls, phosphonates, phosphinates, and combinations thereof. In some embodiments, the functional groups are capable of free-radical polymerization and can include, but are not limited to, ethylenically unsaturated groups such as, for example, allyl, vinyl, acryloyl and methacrylol, and maleate and maleimido; and combinations thereof. In some embodiments, the functional groups include halides. In some embodiments, the functional group may include light scattering groups, magnetic groups, nanogold, other proteins, a solid matrix, radiolabels, carbohydrates, and combinations thereof.

The coating may at least substantially promote development of the functional endothelium as the source of the thrombomodulin when compared to a control development of such endothelium formation observed following implantation of a metal or polymer drug-eluting medical device. In some embodiments, the medical device comprises an implant.

One of skill will appreciate that a functional endothelium exists, or is promoted, for example, where the amount of thrombomodulin in the functional endothelium is in a quantity sufficient to show a statistical difference in an amount of thrombus formation when compared to a control development of such an endothelium, or lack thereof, observed following implantation of a control metal or polymer drug-eluting device. In some embodiments, the functional endothelium has been promoted where it can produce an amount of thrombomodulin that is substantially greater than an amount of thrombomodulin observed from a control medical device. An amount of thrombomodulin is "substantially greater" when the desired anti-thrombus effect is statistically improved over that observed from a control medical device. In some embodiments, a functional endothelium exists, or has been promoted, where the desired effects of thrombus inhibition, restenosis inhibition, and/or blood flow improvement from the presence of thrombomodulin becomes statistically observable when compared to a control development of such endothelium formation observed following implantation of a metal or polymer drug-eluting medical device that does not delay the onset of drug-elution for at least 5, 10, 12, 14, 15, 20, 25, 30, 45, 60, 75, or 90 days, or any range therein.

In addition, the coating may at least substantially inhibit development of a hyperproliferative tissue when compared to a control development of such hyperproliferative tissue observed following implantation of a metal or polymer medical device that does not elute a drug. One of skill will appreciate, for example, that hyperproliferative tissue growth includes a growth of tissue beyond what is normal and healthy. It can cause adverse effects on the function or physiology of the subject.

The inhibition of the development of a hyperproliferative tissue can occur, or be promoted, when the amount of such tissue is in a quantity sufficient to show a statistical difference in an amount of tissue formation when compared to a control development of such an tissue, or lack thereof, observed following implantation of a control metal or polymer medical device that does not elute a drug. In some embodiments, the amount of hyperproliferative tissue produced from the control device is substantially greater than an amount of tissue observed from a medical device having a coating taught herein. An amount of tissue can be considered "substantially greater" when the measured amount is statistically greater. In some embodiments, restenosis is inhibited by at least 5, 10, 12, 14, 15, 20, 25, 30, 45, 60, 75, 90, 95, 99, 100 percent, or any amount therein, when compared to a control development of such restenosis formation observed following implantation of a metal or polymer medical device that does not elute a drug.

The coatings can be designed for a predetermined delay time and release rate of the drug. As described above, layers and sub-layers of coatings can be designed to have a different composition to impart more control over drug elution, coating hydrolysis, coating strength and integrity, other physical traits, and other such coating characteristics known to one of skill. In some embodiments, for example, the drug-reservoir layer can further comprise an accelerant layer to accelerate the time to onset of drug elution. In fact, in some embodiments, the accelerant layer can have a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons.

And, as described above, other variables, such as layer or sub-layer thickness, and/or thickness ratios between layers and/or sub-layers, can be used to obtain a desired delay time for drug release, release rate of the drug, fluid uptake in the coating, as well as coating strength, integrity, and the like. In some embodiments, the thickness of the coating can range from about 2 microns to about 9 microns, from about 1 micron to about 40 microns, from about 1 micron to about 30 microns, from about 2 microns to about 38 microns, from about 3 microns to about 36 microns, from about 4 microns to about 34 microns, from about 5 microns to about 7 microns, from about 4 microns to about 6 microns, or any range therein. In some embodiments, the thickness of the coating is less than 12 microns, less than 11 microns, less than 9 microns, less than 8 microns, less than 7 microns, less than 6 microns, less than 5 microns, or any range therein, such as, for example, from 7 microns to 12 microns, 9 microns to 12 microns, or 7 microns to 9 microns. In some embodiments, each layer or sub-layer can range from about 0.1 micron to about 10 microns, from about 0.1 micron to about 7 microns, from about 0.1 micron to about 5 microns, from about 0.1 micron to 3 microns, from about 0.1 micron to about 2 microns, from about 0.1 micron to about 0.9 microns, from about 0.1 micron to about 0.8 microns, from about 0.1 micron to about 0.7 microns, from about 0.1 micron to about 0.6 microns, from about 0.1 micron to about 0.5 microns, from about 0.1 micron to about 0.4 microns, from about 0.1 micron to about 0.3 microns, from about 0.3 micron to about 0.8 microns, from about 0.2 microns to about 5 microns, from about 0.2 microns to about 4 microns, from about 0.3 microns to about 3 microns, from about 0.5 microns to about 5 microns, from about 0.6 microns to about 3 microns from about 1 micron to about 3 microns, or any range therein.

In some embodiments, for example, the thickness ratio of the drug-reservoir layer to the drug-containing layer can range from about 4:1 to about 10:1, from about 4:1 to about 7:1, from about 2:1 to about 12:1, from about 3:1 to about 11:1, from about 5:1 to about 10:1, from about 2:1 to about 8:1, from about 4:1 to about 6:1, or any range therein. In some embodiments, the ratio can be a mass ratio, where the mass of the drug-reservoir layer to the mass of the drug-containing layer can range from 3:1 to 20:1, from 4:1 to 16:1, from 5:1 to 15:1, from 6:1 to 10:1, or any range therein.

In some embodiments thinner coatings and desired ratios can be achieved using higher percentages of drug in the drug-containing layer, where in some embodiments, the drug-containing layer is composed of 100, 99, 98, 97, 96, 95, 94, 93, 92, 91, 90 percent drug, or any range therein. The drug-containing layer can range from about 0.05 to about 5 microns, from about 0.03 to about 3 microns, from about 0.1 to about 2 microns, or any range therein in thickness, in some embodiments.

The relative hydrophobicity or hydrophilicity can also impart desired drug retention and elution behavior from the coating. For example, the miscibility of the drug in a coating can be preselected to affect the rate of drug migration in the coating, and/or elution from the coating. In some embodiments, the drug can be selected to be miscible in a coating to increase retention time in the coating. Likewise, in some embodiments, the drug can be selected to be less miscible, or immiscible, in a coating to decrease retention time in the coating.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

One of skill will appreciate that a coating can be applied using any one, or any combination, of methods known in the art, where the terms "form" and "apply" can be used interchangeably, in some embodiments. The compositions can be in the form of coatings for medical devices such as, for example, a balloon-expandable breast implant. There are many coating configurations possible, and each configuration can include any number and combination of layers. In some embodiments, the coatings can comprise one or a combination of the following four types of layers: (a) an agent layer, which may comprise a polymer and an agent or, alternatively, a polymer free agent; (b) an optional primer layer, which may improve adhesion of subsequent layers on the implantable substrate or on a previously formed layer; (c) an optional topcoat layer, which may serve as a way of controlling the rate of release of an agent; and (d) an optional biocompatible finishing layer, which may improve the biocompatibility of the coating.

In some embodiments, any one or any combination of layers can be used. And, each layer can be applied to an implantable substrate, for example, by any method including, but not limited to, dipping, spraying, pouring, brushing, spin-coating, roller coating, meniscus coating, powder coating, inkjet-type application or a combination thereof. In one example, each of the layers can be formed on an implant by dissolving one or more biodegradable polymers, optionally with a non-biodegradable polymer, in one or more solvents and either (i) spraying the solution on the implant or (ii) dipping the implant in the solution. In this example, a dry coating of biodegradable polymer may be formed on the implant when the solvent evaporates.

The formation of each layer may involve use of a casting solvent. A casting solvent is a liquid medium within which a polymer can be solubilized to form a solution that may be applied as a coating on a substrate. The casting solvent must be selected to avoid adversely affecting an underlying material such as, for example, an underlying primer layer or a bare implant structure. In one example, a material used to form the primer layer is soluble in a highly polar casting solvent but is reasonably insoluble in a low polarity casting solvent. A material is "reasonably insoluble" in a solvent when the material does not solubilize to an extent great enough to significantly affect the performance of the resulting product, meaning that the product can still be used for its intended purpose. In this example, an overlying agent layer that is soluble in a low polarity casting solvent can be applied to the underlying primer layer without disrupting the structure of primer layer.

The casting solvent may be chosen based on several criteria including, for example, its polarity, ability to hydrogen bond, molecular size, volatility, biocompatibility, reactivity and purity. Other physical characteristics of the casting solvent may also be taken into account including the solubility limit of the polymer in the casting solvent, the presence of oxygen and other gases in the casting solvent, the viscosity and vapor pressure of the combined casting solvent and polymer, the ability of the casting solvent to diffuse through an underlying material, and the thermal stability of the casting solvent.

One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, InC) (10:40:50 w/w); and 1,1,2-trichloroethane and chloroform (80:20 w/w).

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures.

A medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30 degrees C. to about 200 degrees C., from about 35 degrees C. to about 190 degrees C., from about 40 degrees C. to about 180 degrees C., from about 45 degrees C. to about 175 degrees C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. The amount of mobilization of the drug can be considered "substantially inhibited" when the measured amount of mobilization of the drug from the drug-containing layer is statistically less than if the drying procedure was not used as taught herein.

The application of the sub-layers can be used to at least substantially promote a retention of the drug in the drug-containing layer during formation of the coating when compared to such a coating without the application of the sub-layers. The amount of retention of the drug can be considered "substantially promoted" when the measured amount of retention of the drug from the drug-containing layer is statistically greater than if the sub-layer application as taught herein was not used.

In some embodiments, the drug-retaining layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-retaining layer, is more hydrophilic than the remainder of the drug-retaining layer, and comprises at least one sub-layer having a thickness of less than or equal to 3 microns, where a repeated application the sub-layer is used to form thicknesses of greater than 3 microns. The accelerant layer can contain some of the drug. In some embodiments, the drug composes less than 30, 25, 20, 15, 10, 7, 5, 4, 3, 2, 1 percent, or any amount therein, of the accelerant layer. And, in some embodiments the drug composes less than 10 percent of the accelerant layer.

The coatings can be heterogeneous in morphology. For example, a hydrophobic layer can contain hydrophilic regions. Likewise, a more hydrophilic coating can have hydrophobic regions. The hydrophilic regions can be in the form of isolated packages of material, or "islands" in some embodiments, where the isolated hydrophilic package can add to the water absorption rate, and thus hydrolysis rate, of the coating. The isolated packages may be added during the coating process as droplets, in some embodiments. The coatings taught herein can, in some embodiments, further comprise pockets of hydrophilic material in the drug-retaining layer, wherein the hydrophilic material can comprise a second drug. There can be one or more such pockets, and the pockets can be positioned anywhere throughout the coating. In some embodiments, one or more hydrophilic pockets are positioned in the drug reservoir layer and, in some embodiments, one or more hydrophilic pockets are positioned in the drug-retaining layer. In some embodiments, the hydrophilic pockets comprise a drug selected from the group consisting of dextran, heparin, ticlopidine, chlopidogrel, enoxaparin, dalteparin, hirudin, bivalirudin, argatroban, and danparoid.

The coating can be applied to a surface of a medical device using, for example, wet chemistry and acetone as a solvent with techniques known to one of skill. At least one drug and polymer is dissolved into the volatile solvent to form a drug solution, and the drug can be an anti-proliferative, such as rapamycin. The volatile solvent can be acetone, dichloromethane, or a mixture of the two solvents.

In one example, about 1-2 micron of a drug-containing layer can be covered with a 1-3 micron accelerant layer made of acid terminated 75/25 monomer ratio PLGA having a molecular weight of 90-120 KDalton, and the accelerant layer can be covered with about 6-12 microns of ester terminated 75/25 monomer ratio PLGA having a molecular weight of 100-160 KDalton. This unique and novel combination of compositions in different layers, as well as the relative thicknesses and positioning of the layers, can provide a coating having a desired delay in the onset of drug elution. The elution, in fact, can be delayed for a designed, prolonged period of time, at which time the drug release is fast enough to have a therapeutic effect. The coating is robust, maintaining functional integrity through stresses and strains of assembly and deployment. And, the coating can maintain a low enough profile of the implant for ease of delivery and introducing less foreign material into the body.

The following is an example of a process that can be used to create composite elution layers, a process comprising multiple sub-layer applications, such as those described herein. The drug is added to the solvent for wet chemistry application, and the drug-containing layer may be applied to the surface of the device. The drug-containing layer can be 120 nanometers and 6 microns, 200 nanometers and 3 microns, 0.7-1.1 microns, or any range therein, thick in some embodiments. The drug-containing layer is then dried with convection of a non reactive gas, such as nitrogen, at a temperature elevated above room temperature.

The accelerant layer polymer is mixed with a solvent for wet chemistry application, and the accelerant layer is created by layering multiple sub-layers of the same material. Each sub-layer is coated onto previous layer and dried with convection of gas as described in above using a drying time of about 1-2 hours before coating the next sub-layer/layer. The accelerant layer can be about 1-2 microns thick and composed of 50:50 PLGA with acid terminal end-groups. In some embodiments, the accelerant layer can be about 3-5 microns thick and composed of 2-3 sub-layers of 75:25 PLGA with acid terminal end-groups. And, in some embodiments, the accelerant layer can be between about 120 nanometers and 6 microns, 400 nanometers and 4 microns, 500 nanometers and 5 microns, or any range therein. Moreover, the concentration of the drug in the accelerant layer can be less than 50% of the drug-containing layer before implantation in some embodiments.

The drug-retaining layer can then be prepared and coated onto the accelerant layer and dried. The drug-retaining layer is applied by layering multiple sub-layers of the same material. Each sub-layer is coated onto previous layer and dried using convection of gas as described above with drying times of about 1-2 hours before coating the next sub-layer/layer. The drug-retaining layer can be about 3-5 times the thickness of the accelerant layer, in some embodiments, if the accelerant layer is composed of 50:50 PLGA having an ester terminal end-group in some embodiments. In some embodiments, the thickness of the drug-retaining layer can be about 0.2-2 times that of the accelerant layer, if the accelerant layer is composed of 75:25 PLGA having an ester terminal end-group. The entire assembly may then be packaged and sterilized for deployment.

One of skill will appreciate that any non-reactive or substantially non-reactive gas can be used including, but not limited to, nitrogen, carbon dioxide, or a noble gas. The heated gas's temperature can be, for example, between about 70 degrees F. and the drug's melting point. In some embodiments, the gas's temperature can be between about 70 degrees F. and 240 degrees F., from 140-190 degrees F., or any range therein. The specified drying time can be, for example, between about 0 minutes and 3 hours, 10-30 minutes, 30 minutes and 1 hour, 15 minutes and 2 hours, or any range therein. The gas surface flow rate can be between about 40 and 500 inches per second, 50 and 400 inches per second, 100 and 500 inches per second, or any range therein. In some embodiments, the gas surface flow rate is 90-150 inches/seC It should be appreciated that, in some embodiments, the term "agent" or "drug" can be used interchangeably. An "agent" or "drug" can be a moiety, for example, that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical articles that can be improved through the teachings described herein are within the scope the invention.

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to, many of the polymers listed above such as, for example, carboxymethylcellulose; poly(alkylene glycols) such as, for example, PEG; poly(N-vinyl pyrrolidone); poly (acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD). In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the teachings herein include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin I1, actinomycin X1, actinomycin C1, and dactinomycin (COSMEGEN, Merck & Co., InC). Antineoplastics or antimitotics include, for example, paclitaxel (TAXOL, Bristol-Myers Squibb Co.), docetaxel (TAXOTERE, Aventis S.A.), methotrexate, azathioprine, vincristine, vinblastine, fluorouracil, doxorubicin hydrochloride (ADRIAMYCIN, Pfizer, InC) and mitomycin (MUTAMYCIN, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethyl ketone (synthetic antithrombin), dipyridamole, glycoprotein IIb/IIIa platelet membrane receptor antagonist antibody, recombinant hirudin, and thrombin inhibitors (ANGIOMAX, Biogen, InC), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINIVIL and PRINZIDE, Merck & Co., InC); calcium channel blockers such as nifedipine; colchicines; fibroblast growth factor (FGF) antagonists, fish oil (omega 3-fatty acid); histamine antagonists; lovastatin (MEVACOR, Merck & Co., InC); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST, Santen, InC), and any prodrugs, metabolites, analogs, homologues, congeners, derivatives, salts and combinations thereof.

Other bioactive agents useful in the teachings herein include, but are not limited to, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs; estradiol; clobetasol; idoxifen; tazarotene; alpha-interferon; host cells such as epithelial cells; genetically engineered epithelial cells; dexamethasone; and any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof. The drugs eluted from the coatings taught herein can function as an anti-proliferative or immunosuppressant. In some embodiments, the drug can be rapamycin or a derivative of rapamycin. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, and estradiol. One of skill will appreciate that agents that affect vascular smooth muscle cell (VSMC) proliferation or migration can also be used in some embodiments, including, but not limited to transcription factor E2F1.

The agents of the present invention can be used alone or in combination with other agents to obtain other desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject in a desired amount to obtain a desired effect. In some embodiments, the desired amount is termed an "effective amount," where the amount administered elicits a desired response. In some embodiments, the effective amount can be a "therapeutically effective amount", administered in an amount that prevents, inhibits, or ameliorates the symptoms of a disease.

It is to be appreciated that the design of a composition for drug release can be dependent on a variety of factors such as, for example, the therapeutic, prophylactic, ameliorative or diagnostic needs of a patient or condition. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In some embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and any range therein, where the percentage is based on the total weight of the polymer and agent or combination of agents.

The medical devices discussed herein can be any devices known to one of skill to benefit from the teachings provided. A medical device, for example, can be comprised of a metal or an alloy, including, but not limited to, ELASTINITE, NITINOL, stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY, Elgiloy Specialty Metals, InC; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that, are comprised of bioabsorbable polymers or biostable polymers are also included within the scope of the present invention.

The terms "plasticizer" and "plasticizing agent" can be used interchangeably in the teachings herein, and refer to any agent, including any agent described above, where the agent can be added to a polymeric composition to modify the mechanical properties of the composition or a product formed from the composition. Plasticizers can be added, for example, to reduce crystallinity, lower the glass-transition temperature (Tg), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters;

organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methylpyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight.

The amount of plasticizer used in the teachings herein, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents.

It should be appreciated that any one or any combination of the plasticizers described above can be used in the teachings herein. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

One embodiment applies gamma irradiation or electron beam (e-beam) sterilization. Other types of radiosterilization can be used.

In some embodiments, the drug-containing layer may be applied to a surface of a prosthesis, and the drug-reservoir layer may be applied on or over the drug layer. In some embodiments, the prosthesis can comprise a fitting for mechanically coupling to an adjacent tissue, such as calcified or soft tissue, for example, a bone implant or intra-organ implant. In some embodiments, the system may comprise an entirely resorbable construct, such as a capsule, a tablet, a pellet, a shaft, a rod, a sphere, disc, or a ring. In some embodiments, the resorbable construct may be configured for deployment in an anatomic environment such as the gastrointestinal tract, a synovial joint, a cardiovascular lumen, a cardiovascular chamber, a urinary lumen, a urinary chamber, a reproductive lumen, a reproductive chamber, a gynecological lumen, a gynecological chamber, an endocrine lumen, or an endocrine chamber.

In one example, a tubular drain system can be implanted, leading from one of the ventricles of the brain to an abdominal position. One or more portions, or all, or the drain system may be coated and configured to promote endothelization/healing by substantially blocking elution of antiproliferative drugs, before controllably eluting drugs to prevent excessive fibrous cellular encapsulation and/or stenosis.

In another example, portions of a "venous" needle or "arterial" needle in an arteriovenous fistula may be coated and configured to promote endothelization/healing by substantially blocking elution of antiproliferative drugs, before controllably eluting drugs to prevent stenosis and/or excessive cellular encapsulation. Many transcutaneous port or cannulation device configurations may be so treated.

In another example, portions of pacemaker, defibrillator, or other implantable device leads, such as a distal portion configured to engage a portion of the endocardial wall, may be coated and configured to promote endothelization/healing by substantially blocking elution of antiproliferative drugs, before controllably eluting drugs to prevent excessive cellular encapsulation.

In another example, portions of an intraocular lens prosthesis, such as the main body or legs of the prosthesis may be coated and configured to promote endothelization/healing by substantially blocking elution of antiproliferative drugs, before controllably eluting drugs to prevent excessive cellular encapsulation.

In another example, portions of a bile duct or other duct, tube, vessel, or lumen prosthesis may be coated and configured to promote endothelization/healing by substantially blocking elution of antiproliferative drugs, before controllably eluting drugs to prevent stenosis and/or excessive cellular encapsulation.

In another example, pellets or small prostheses used to treat tissue volumes such as those of a prostate gland may be coated and configured to promote endothelization/healing by substantially blocking elution of antiproliferative drugs, before controllably eluting drugs.

In another example, immunosuppressants and/or cytotoxics, such as taxol, can be delivered in such devices to aid in the treatment of tumors, such as prostate or other tumors. Pellets containing such drugs, for example, may be delivered through the urethra or by other surgical means.

In another example, severed nerve portions may be joined with a graft comprising an outer sheath of coated drug eluting material configured to protect and isolate the inner graft material while also promoting endothelization/healing by substantially blocking elution of antiproliferative drugs, before controllably eluting drugs to discourage excessive cellular overgrowth which may lead to nerve impingement and/or adhesion.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims. In accordance with another aspect, the fastener portion is formed monolithic with the head portion, as controlled by a computer so that the fastener/head portion conforms to the patient's body for better fit.

In yet another embodiment, the fastener portion is mounted for movement relative to the head portion. In this regard, the head portion defines a central axis oriented perpendicular to the spinal rod channel and the fastener portion is mounted for angular movement relative to the central axis of the head portion. More particularly, the fastener portion includes a generally spherical head and a threaded body which depends from the spherical head, and the head portion defines a seat to accommodate the spherical head and an aperture to accommodate the threaded body. In use, upon rotation of the upper portion of the locking cap relative to the lower portion of the locking cap into a locked position, the position of the head portion relative to the spinal rod and the position of the fastener relative to the head portion become fixed.

It should be recognized that the subject disclosure is not limited in any way to the illustrated bone screw and right-angle hook. Rather, these particular fasteners are merely examples of the type of devices that can employ the novel locking cap disclosed herein. Other fasteners commonly utilized in spinal stabilization systems, such as, for example, hooks having alternative angular geometries as well as clamps are also envisioned. Indeed, it is envisioned that any component designed for attachment to an elongated spinal rod or transverse coupling rod, may incorporate the novel locking cap of the subject disclosure. Also, any number of fastening devices can be applied along the length of the spinal rod.

An embodiment of the invention can be used where two or more segments of bone need to be aligned and require flexibility and changes of material properties based on temperature when device is placed.

An embodiment of the invention can help with broken bones, trauma, or other types of surgery but also building design or transportation design.

All references, patents, patent applications or other documents cited are hereby incorporated by reference herein in their entirety.

A natural feel is achieved through viscoelastic harmony of properties between the existing tissue and the implant. This can be done by manipulating the viscous component of the implant through flow properties by way of the particle size and particle size distribution ratios. The elastic component is intrinsic within the material tertiary structure (molecular weight and steric hindrance) and cross linking densities. The interpenetrating polymer network hydrogels have a number of desirable properties. These properties include high tensile strength with high water content, making the interpenetrating polymer network hydrogels excellent for use in dermal filling applications. Other advantages and features include: longevity without touch up, hyper-volumic degradation, anatomic compliant and iso-osmotic controlled, among others.

The present invention has been described particularly in connection with a breast, butt, or body implant, among others, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not by the specific disclosure herein, but only by the appended claims. The other methods, used for characterization of the products according to one embodiment are described in the following examples which illustrate preferred embodiments of one embodiment without, however, being a limitation thereof.

Variations and modifications can, of course, be made without departing from the spirit and scope of the invention.

What is claimed is:

1. A method to protect a medical device from scarring a body after implanting the device in the body, comprising:
    swelling a device shell;
    allowing hyaluronic acid (HA) to diffuse into a polymer matrix of the shell;
    cross-linking the HA while the shell is swollen; and
    deswelling the device shell thereafter.

2. The method of claim 1, comprising forming an interpenetrating network with the HA.

3. The method of claim 1, comprising cross-linking the HA to an iso-osmotic state.

4. The method of claim 1, comprising swelling the device shell with tetrahydrofuran (THF) or dichloromethane (DCM).

5. The method of claim 1, comprising deswelling with water or saline.

6. The method of claim 1, comprising cross-linking the HA with divinyl sulfide (DVS) or diglycidyl ether (BDDE).

7. The method of claim 1, wherein the device comprises an implantable medical device.

8. The method of claim 1, wherein the device comprises a breast implant, a facial implant, a heart valve, a stent, a graft, a cardiovascular graft, an artificial joint, a rod, a knee portion, a skull plate, cranial facial hardware, a heart part, a pacemaker, an electrical lead, a nerve stimulator, a suture.

9. A method to protect a medical device from scarring a body after implanting the device in the body, comprising:
    swelling a device shell;
    allowing hyaluronic acid (HA) to diffuse into a polymer matrix of the shell;
    cross-linking the HA while the shell is swollen; and
    deswelling the device shell thereafter; and
    preventing capsular contracture after implanting the device in the body.

10. The method of claim 9, wherein the device comprises an implantable medical device.

11. The method of claim 9, wherein the device comprises a breast implant, a facial implant, a heart valve, a stent, a graft, a cardiovascular graft, an artificial joint, a rod, a knee portion, a skull plate, cranial facial hardware, a heart part, a pacemaker, an electrical lead, a nerve stimulator, a suture.

12. A method to protect a medical device from scarring a body after implanting the device in the body, comprising:
    exposing a device surface to hyaluronic acid (HA) or polyethylene glycol (PEG);
    cross linking the HA or PEG;
    swelling a device shell;
    allowing HA or PEG to diffuse into a polymer matrix of the shell; and
    deswelling the device shell thereafter.

13. The method of claim 12, wherein the device comprises an implantable medical device.

14. The method of claim 12, wherein the device comprises a breast implant, a facial implant, a heart valve, a stent, a graft, a cardiovascular graft, an artificial joint, a rod, a knee portion, a skull plate, cranial facial hardware, a heart part, a pacemaker, an electrical lead, a nerve stimulator, a suture.

15. The method of claim 12, comprising cross-linking the HA while the shell is swollen.

* * * * *